(12) United States Patent
Cindrich et al.

(10) Patent No.: US 7,670,317 B2
(45) Date of Patent: Mar. 2, 2010

(54) ONE PIECE LOW DRAG SEPTUM

(75) Inventors: Chris Cindrich, South Jordan, UT (US); Greg L. Brimhall, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 9 days.

(21) Appl. No.: 11/258,560

(22) Filed: Oct. 25, 2005

(65) Prior Publication Data
US 2007/0093778 A1    Apr. 26, 2007

(51) Int. Cl.
*A61M 5/178*    (2006.01)
(52) U.S. Cl. ................................. 604/167.01
(58) Field of Classification Search .............. 604/256, 604/195, 167.01, 167.02, 167.03, 167.04, 604/167.06, 533, 536
See application file for complete search history.

(56) References Cited

U.S. PATENT DOCUMENTS

| | | | |
|---|---|---|---|
| 5,135,504 A | 8/1992 | McLees | |
| 5,215,525 A | 6/1993 | Sturman | |
| 5,215,528 A | 6/1993 | Purdy et al. | |
| 5,312,359 A | 5/1994 | Wallace | |
| 5,328,482 A | 7/1994 | Sircom et al. | |
| 5,447,501 A | 9/1995 | Karlsson et al. | |
| 5,458,658 A | 10/1995 | Sircom | |
| 5,509,912 A * | 4/1996 | Vaillancourt et al. | 604/537 |
| 5,562,631 A | 10/1996 | Bogert | |
| 5,562,633 A | 10/1996 | Wozencroft | |
| 5,573,510 A | 11/1996 | Isaacson | |
| 5,575,769 A * | 11/1996 | Vaillancourt | 604/86 |
| 5,584,809 A | 12/1996 | Gaba | |
| 5,599,310 A | 2/1997 | Bogert | |
| 5,601,536 A | 2/1997 | Crawford et al. | |
| 5,690,619 A | 11/1997 | Erskine | |
| 5,697,907 A | 12/1997 | Gaba | |
| 5,699,821 A * | 12/1997 | Paradis | 137/1 |
| 5,700,250 A | 12/1997 | Erskine | |
| 5,704,919 A | 1/1998 | Kraus et al. | |
| 5,718,688 A | 2/1998 | Wozencroft | |
| 5,749,856 A | 5/1998 | Zadini et al. | |
| 5,810,780 A | 9/1998 | Brimhall et al. | |
| 5,843,046 A * | 12/1998 | Motisi et al. | 604/256 |
| 5,853,393 A | 12/1998 | Bogert | |

(Continued)

OTHER PUBLICATIONS

PCTUS0641836-International Search Report.

*Primary Examiner*—Nicholas D Lucchesi
*Assistant Examiner*—Christopher D Koharski
(74) *Attorney, Agent, or Firm*—Mony R. Ghose; Craig Metcalf; Kirton & McConkie

(57) ABSTRACT

A one-piece low drag septum is provided for preventing escape of fluid from an introducer needle during removal of such a needle from a catheter and introducer needle assembly. The septum generally includes a distal portion, a proximal portion, a cavity portion, and a longitudinal axis. The distal portion acts as a primary seal to prevent escape of blood from the catheter into the assembly and is generally positioned furthest away from the user of the apparatus and nearest the patient. The cavity portion reduces friction placed on the introducer needle. The proximal portion of the septum acts as a secondary seal to prevent escape of material from the cavity, seals the cavity, and wipes the needle as it is being withdrawn from the catheter assembly.

6 Claims, 17 Drawing Sheets

U.S. PATENT DOCUMENTS

| | | |
|---|---|---|
| 5,882,345 A * | 3/1999 | Yoon .................. 604/264 |
| 5,935,109 A | 8/1999 | Donnan |
| 5,935,110 A * | 8/1999 | Brimhall ............ 604/167.06 |
| 6,056,726 A | 5/2000 | Isaacson |
| 6,077,244 A | 6/2000 | Botich et al. |
| 6,206,851 B1 | 3/2001 | Prosi |
| 6,221,047 B1 | 4/2001 | Greene et al. |
| 6,224,569 B1 | 5/2001 | Brimhall |
| 6,287,278 B1 | 9/2001 | Woehr et al. |
| 6,379,332 B1 | 4/2002 | Van Landuyt |
| 6,461,362 B1 | 10/2002 | Halseth et al. |
| 6,506,181 B2 | 1/2003 | Meng et al. |
| 6,595,954 B1 | 7/2003 | Luther et al. |
| 6,616,630 B1 | 9/2003 | Woehr et al. |
| 6,652,486 B2 | 11/2003 | Bialecki et al. |
| 6,663,592 B2 | 12/2003 | Rhad et al. |
| 6,689,102 B2 | 2/2004 | Greene |
| 6,695,814 B2 | 2/2004 | Greene et al. |
| 6,709,419 B2 | 3/2004 | Woehr |
| 6,719,726 B2 | 4/2004 | Meng et al. |
| 6,749,588 B1 | 6/2004 | Howell et al. |
| 2003/0083620 A1 | 5/2003 | Luther et al. |
| 2004/0078003 A1 | 4/2004 | Smith et al. |
| 2004/0092889 A1 | 5/2004 | Ferguson et al. |
| 2004/0193112 A1 | 9/2004 | Glazier et al. |
| 2004/0225260 A1 | 11/2004 | Villa et al. |
| 2004/0243060 A1 | 12/2004 | Rossi et al. |
| 2004/0243061 A1 | 12/2004 | McGurk |

* cited by examiner

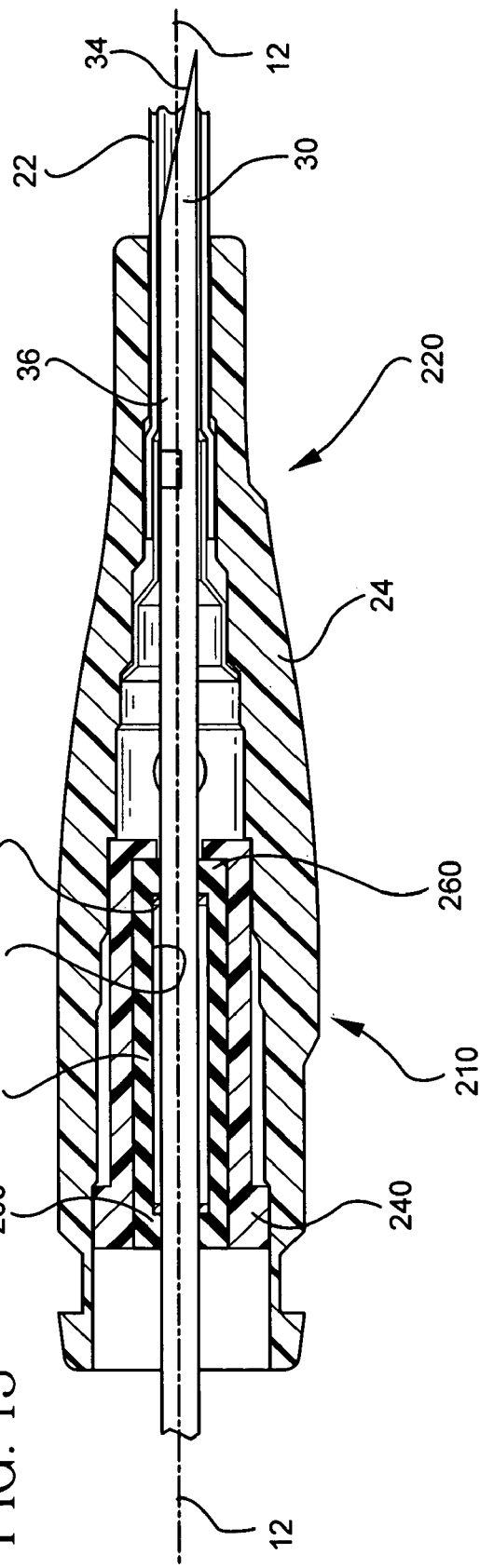
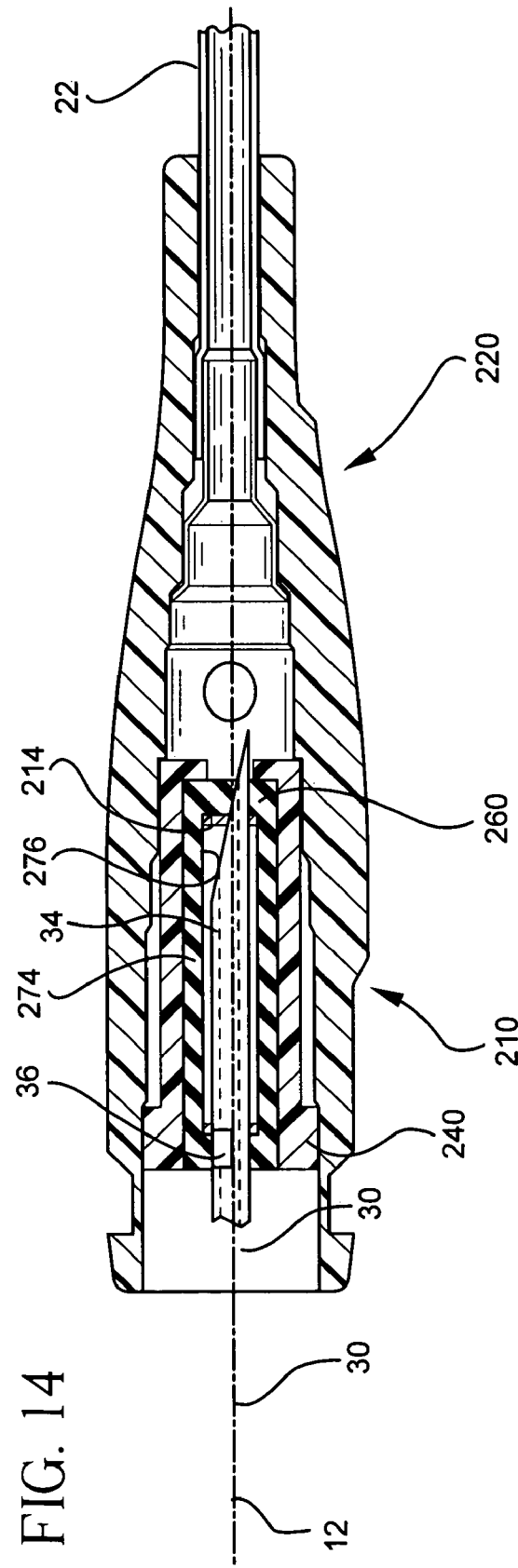

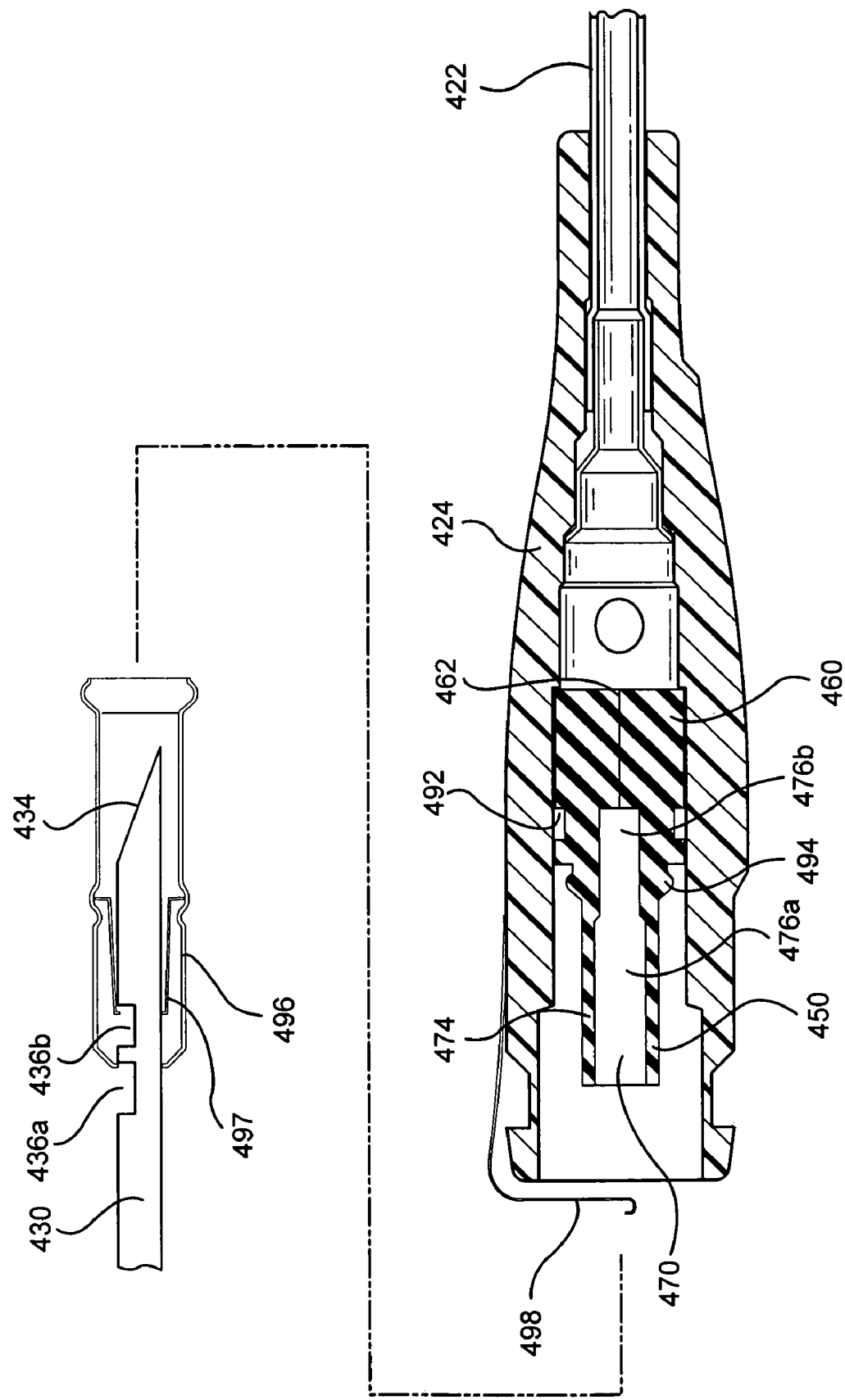

ONE PIECE LOW DRAG SEPTUM

BACKGROUND OF THE INVENTION

The present invention relates to catheter and introducer needle assemblies. In medicine, such catheter and introducer needle assemblies are used to place a catheter properly into the vascular system of a patient. Once in place, catheters such as intravenous (or "IV") catheters may be used to infuse fluids including normal saline, medicinal compounds, and/or nutritional compositions (including total parenteral nutrition, or "TPN") into a patient in need of such treatment. Catheters additionally enable the removal of fluids from the circulatory system and monitoring of conditions within the vascular system of the patient.

One type of commonly-used catheter is a peripheral intravenous catheter. These short, indwelling intravenous catheters are often used to provide an entry route for medications, fluid for hydration, and in some cases, for parenteral feeding, into a patient. Such catheters are generally short in length, ranging from about one-half to about three inches in length, and are generally made of flexible biocompatible materials. In some cases, these catheters additionally include a radiopaque compound such as barium sulfate to allow the location of the catheters to be tracked once inside the body.

Peripheral IV catheters are often provided as "over-the-needle" catheters mounted over an introducer needle with a sharp distal tip. This sharp tip often includes a bevel intended to be oriented away from the patient's skin during penetration of the skin. A portion of the catheter including at least the distal tip of the catheter securely grips the outside of the needle to prevent catheter peelback during insertion of the catheter into the circulatory system of the patient. Although several techniques for placing such catheters are practiced in the art, many generally include the step of inserting at least a portion of the needle into the target vessel and then sliding the catheter over the needle into place.

The medical worker then attempts to verify proper placement of the catheter within the blood vessel. Catheter and introducer needle assemblies have been provided that include means for verifying proper placement of the catheter in a blood vessel. One such means is a "flashback chamber" that is viewable to the clinician during installation. This chamber receives a small quantity of blood when a vessel is entered, thus allowing observation of blood in the chamber to be an indicator of successful entry into a vessel. Flashback notification may also be provided by providing a notch in the introducer needle a distance from the sharp distal tip of the needle in a region that is housed within the catheter. Blood flashback may then be observed at the notch and regions near it within the catheter when the catheter is at least somewhat transparent.

Once placement of the needle has been confirmed, the user may temporarily occlude flow in the blood vessel at the catheter tip, remove the needle, leaving the catheter in place, and attach a device to the catheter for fluid removal, input, or to seal the catheter. This process has been somewhat difficult in practice since many placement sites simply do not allow easy occlusion of the target vessel. Additionally, even when such occlusion is achieved, it may be imperfect, thus resulting in blood leaking from the catheter, endangering the medical personnel employing it.

Catheter and introducer needle assemblies have thus been provided in the art that provide a variety of seals or "septa" for preventing outflow of fluid during and following removal of the introducer needle. These structures are generally elastomeric plates designed to closely conform to the shape of a needle during storage and use to prevent leaking, then to seal upon removal of the needle. These septa need to be elongated in needles with flashback notches so as to encapsulate the notch and needle tip during needle removal in order to prevent the unwanted escape of blood. This elongation of the septa increases the amount of friction placed on the needle and the amount of effort needed to remove it. In order to overcome this, septa have been developed that include an internal cavity that has an internal diameter slightly larger than that of the needle used. This results in the needle contacting the septum only in regions outside of this cavity, reducing the surface area in contact with the septum.

These septa are currently provided as two-piece components to provide the needed function. They generally include at least two pieces that combine to form the septum with a distal portion, a proximate portion, and a composite cavity. Assembly of these septa has often proven difficult and labor-intensive, however. It would thus be an improvement in the art to provide septa that have fewer parts in order to simplify installation and provide enhanced functionality.

BRIEF SUMMARY OF THE INVENTION

Accordingly, the present invention provides a one-piece septum for use in catheter and introducer needle assemblies. The septum of the invention provides a seal about the introducer needle during storage and use of the needle, and then seals the assembly when the needle is withdrawn to prevent escape of fluid.

The septum of the present invention generally includes distal and proximal portions, a cavity portion, and a longitudinal axis. The distal portion is positioned furthest away from the user of the apparatus and nearest the patient to act as a primary seal and prevent escape of blood from the catheter. The septum also includes a cavity portion which is placed between the distal and proximal portions to reduce friction on the needle. The cavity portion generally has an inner diameter greater than or equal to the outer diameter of the needle used with the septum to reduce friction during removal of the needle. Thus, in some configurations, the septum contacts a needle only at its distal and proximal portions, and in others, it will contact the needle along its length. The proximal portion of the septum acts as a secondary seal to prevent escape of material from the cavity, seals the cavity, and wipes the needle as it is being withdrawn.

The septum of the invention is generally placed in a septum housing which may provide compression to the septum. This housing may be a separate component or may instead be a region of the catheter adapter. The septum housing may be a canister that provides radial compression. Radial compression from the housing helps to assure compliance of the septum to the shape of a needle inserted therethrough and a tight seal upon withdrawal of the needle. The septum may be held in place by compression alone, by a mechanical attachment or interlock, and/or by an adhesive as known to one of ordinary skill in the art. This compression may be from a single radial direction, opposing radial directions, or from a plurality of directions.

The one-piece low drag septum of the invention is provided in a septum assembly for providing a seal about a needle during storage and use, and then sealing closed when the needle is withdrawn. This septum assembly includes a septum housing and a one-piece septum provided therein. The septum has distal and proximal portions, a cavity, and a longitudinal axis. The cavity extends completely through the proximal portion of the septum, and the septum includes at least one flared region extending outwardly away from an outer diameter of the proximal portion. When this septum is inserted into the septum housing, the flared region is compressed, closing the portion of the cavity extending through the proximal portion and providing a seal to a proximal end of the cavity.

Alternatively, the proximal portion of the septum may include two flared portions positioned substantially opposite each other on the outer diameter of the proximal portion. When this septum is installed into a septum housing, radial compression will be provided from the direction of each of the two flared portions. Multiple additional flares may be provided, or alternatively, a circumferential ridge may be used to provide additional radial compression.

The cavity may alternately extend completely through the proximal portion of the septum. In this case, the proximal portion of the septum may include an elongated sheath surrounding a proximal portion of the cavity. The proximal portion of the cavity has an inside diameter equal to or slightly smaller than an outer diameter of the needle in order to grip the needle, act as a seal, and wipe the needle as it exits.

The cavity of the septum of the present invention may alternately not extend completely through either end of the septum. In one such septum, the cavity may extend completely through a first lateral wall and the longitudinal axis of the septum. This produces a cavity that is open to the lateral wall of the septum at a position between its proximal and distal portions. This cavity may be open to a single lateral wall of the septum or to two opposing lateral walls of the septum. This septum could be produced using a side-entry core pin in an injection mold. A septum in which the cavity does not exit either the proximal or distal portions could be produced using gas-assist injection molding technologies.

The septum of the invention may also be made up of at least two longitudinally-hinged segments that are assembled in clamshell fashion. When assembled about an introducer needle and inserted into a septum housing, radial compression keeps the hinged segments of the septum in proper relationship with each other to assure a proper seal. Interlocking features may be provided to assure that this relationship is maintained during installation and use of the septum.

The invention includes catheter and introducer needle assemblies using the one-piece septum of the invention. Such assemblies include a septum assembly and an introducer needle. In some assemblies, the introducer needle includes a flashback notch to allow confirmation of proper placement of the needle. In these, the septum is made longer or equal to than the distance between a proximal end of the notch and the distal end of the needle point opening to assure proper sealing of the needle as it is withdrawn.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 13 is a cross-sectional view of the catheter and introducer needle assembly of FIG. 12 assembled and taken at line 13-13 of FIG. 12 with the introducer needle in place;

FIG. 14 is a cross-sectional view of the catheter and introducer needle assembly of FIGS. 12 and 13 assembled and taken at line 13-13 of FIG. 12 with the introducer needle partially removed;

FIG. 27 is a partially-exploded cross-sectional view of a needle removed from the catheter and introducer needle assembly of FIGS. 23 through 26.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the one-piece low drag septa of the present invention, as represented in FIGS. 1 through 7, is not intended to limit the scope of the invention, as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest from the user wielding the device and closest to the patient.

In portions of the Detailed Description below, the invention is described in connection with a peripheral IV catheter having an integrated extension tube (an "integrated catheter"). It is to be understood that the one-piece low drag septum of the present invention may be used with other catheter systems. The invention may be applicable to standard peripheral IV catheters, extended dwell catheters which require the needle to be connected to the needle hub by a stylet, and other medical devices in which it is desirable to include a septum to regulate the flow of fluid into or out of a space.

Figure 1:
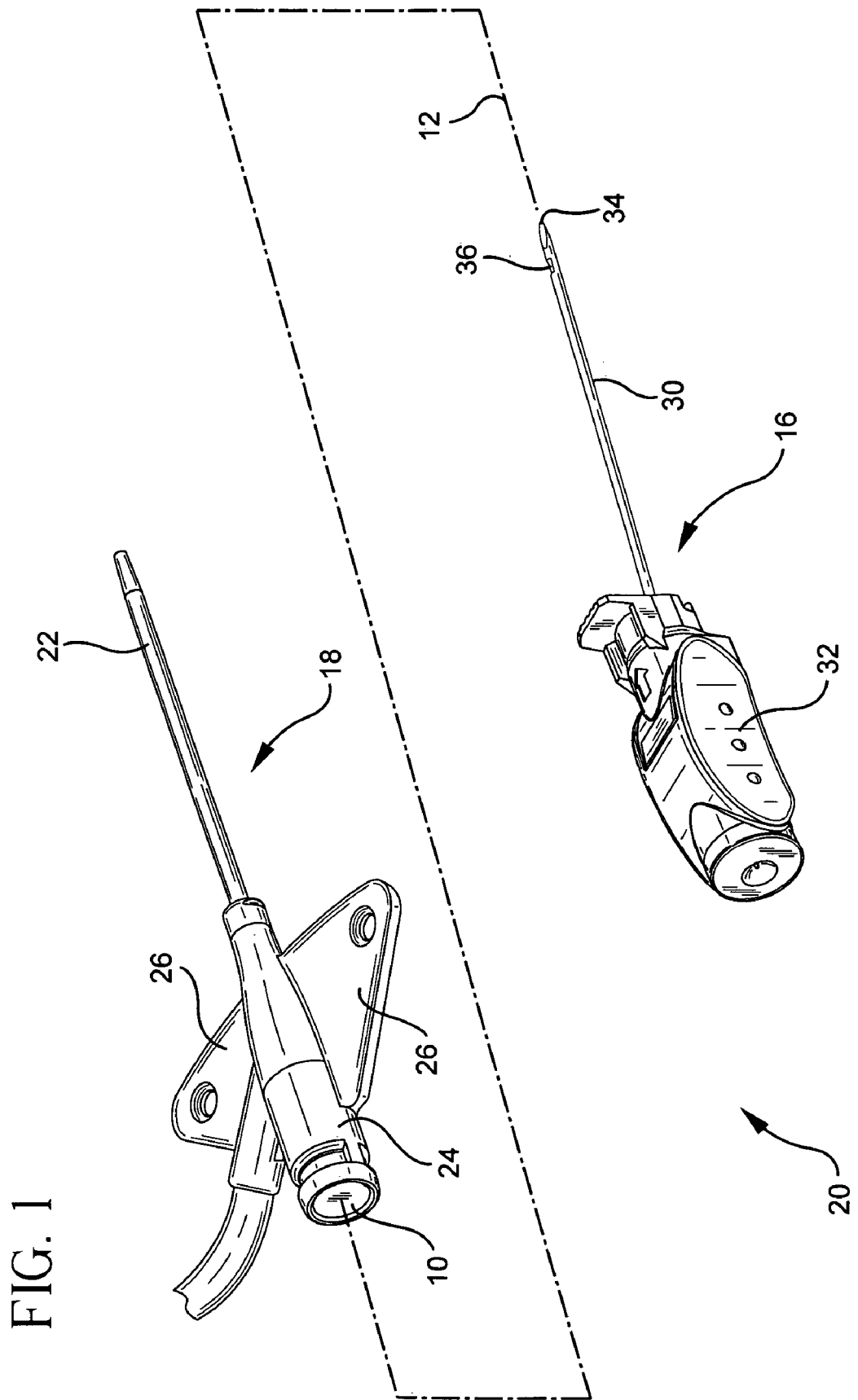
FIG. 1 is a partially exploded perspective view of an integrated catheter and introducer needle assembly incorporating the one-piece low drag septum of the present invention.

An integrated catheter and introducer needle assembly 20 incorporating a one-piece low drag septum 10 of the present invention is illustrated generally in FIG. 1. The catheter and introducer needle assembly 20 includes a catheter assembly 18 including a catheter 22 attached to a catheter adapter 24, as well as a needle assembly 16 having an introducer needle 30 with an axis 12. Catheters 22 may be constructed from materials including, but not limited to, thermoplastic resins such as fluorinated ethylene propylene (FEP), polytetrafluoroethylene (PTFE), and polyurethane. In some embodiments the catheter 22 may be produced from a thermoplastic hydrophilic polyurethane that softens when exposed to the physiological conditions present in a patient's body. It may also be useful to provide catheter 22 in a transparent or translucent form. This enables observation of blood flashback in the annular space between an introducer needle 30 and catheter 22 when the introducer needle 30 includes a notch or opening adjacent to its distal end to allow such blood flow upon successful placement into a blood vessel. The catheter adapter 24 may be produced from materials including, but not limited to, thermoplastic polymeric resins such as polycarbonate, polystyrene, and polypropylene. In some instances it may be useful to produce the catheter adapter 24 from transparent or translucent materials to allow observation of blood flashback within the catheter adapter 24.

The catheter adapter 24 illustrated in FIG. 1 includes wings 26 that extends radially outwardly from either side of catheter adapter 24. The wings 26 simplify handling of the catheter and introducer needle assembly 20 and provide greater surface area for attachment of the catheter 22 to the patient. The wings 26 may optionally include suture holes 28. The proximal end of the catheter 22 is provided with a one-piece low drag septum 10 according to the present invention to prevent escape of fluid from the proximal end of the catheter adapter 24. The catheter 22 and introducer needle assembly 20 further includes an introducer needle 30. The proximal end of the needle 30 is housed in a needle hub 32, while the distal end of the needle 30 has a sharpened tip 34 for piercing the skin of a patient, and a notch 36 to provide flashback of blood upon successful placement of the distal tip 34 into a blood vessel of a patient. In use, the needle 30 and catheter 22 are inserted into a blood vessel of a patient, proper insertion is confirmed, and the needle 30 is removed, leaving the catheter 22 in place.

Figure 2:
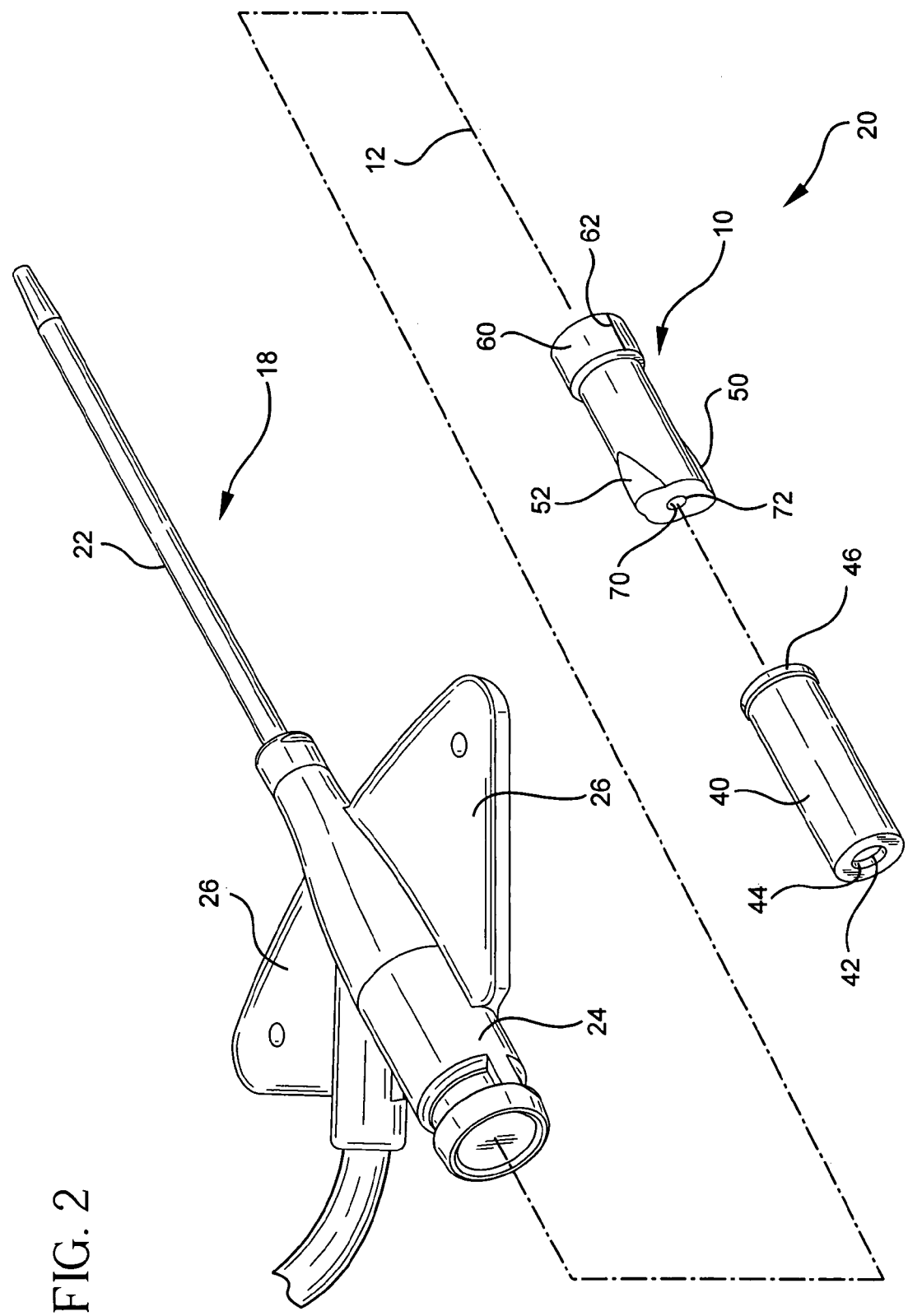
FIG. 2 is a perspective view of the integrated catheter and introducer needle assembly of FIG. 1 showing the form and placement of a first embodiment of the one-piece low drag septum of the present invention.

FIG. 2 is a partially exploded view of the catheter assembly 18 with the septum 10 shown separated from the catheter assembly 18. When assembled, the septum 10 seals the proximal end of the catheter adapter 24 to prevent leakage of fluid from the proximal end of the catheter adapter 24.

The septum 10 of the present invention is a one-piece device adapted to fit within the catheter adapter 24. In some embodiments, the septum 10 is first placed within a septum housing 40. The septum housing 40 has a proximal end with a passage 42 extending through the proximal end of the housing 40 and open to a lumen 44 of the housing. The distal end of the housing 40 is opened wide to receive the septum 10. In other embodiments, however, no separate septum housing component is needed. In these embodiments, the catheter adapter 24 takes the place of the septum housing and retains and provides compressive force to the septum 10. During use of the assembly 20, the septum 10 operates to prevent escape of fluid from the assembly 20 after its insertion into a patient, and then continues to prevent fluid escape when the needle 30 is withdrawn from the patient, leaving the catheter 22 in place.

Figure 3:
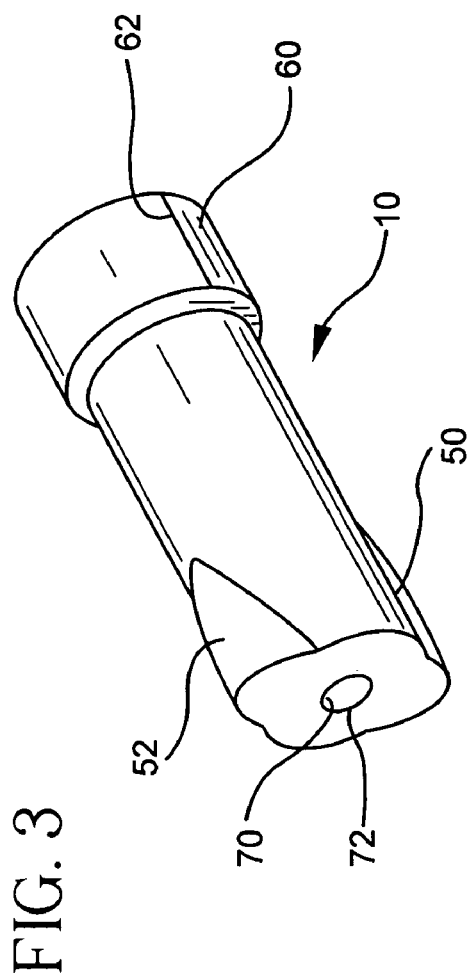
FIG. 3 is an isolated perspective view of the one-piece low drag septum of FIG. 2.
Figure 5:
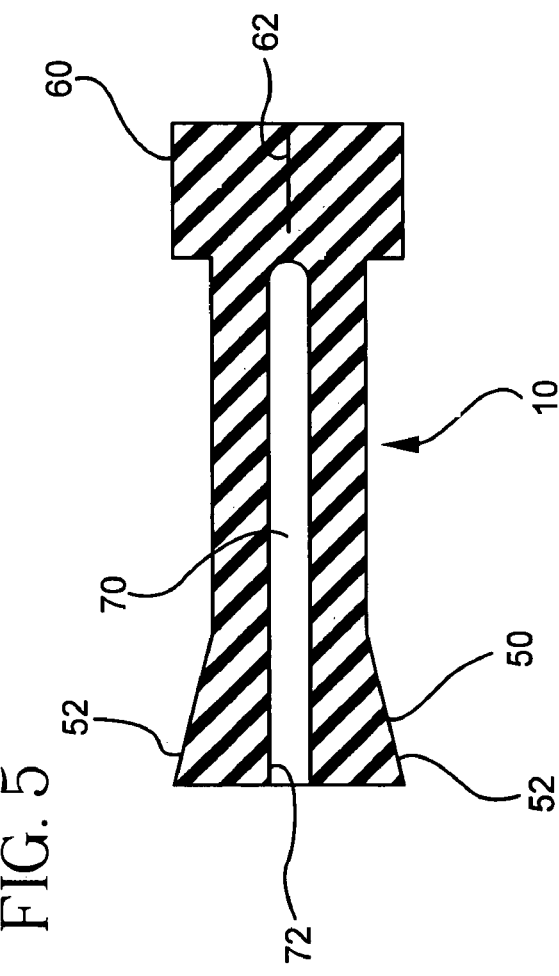
FIG. 5 is a cross-sectional view of the one-piece low drag septum of FIG. 3 taken at line 5-5 of FIG. 4.

FIGS. 3-7 show the septum 10 of FIGS. 1 and 2 (and minor variants thereof) isolated, and viewed from an end, or in cross-section, as discussed in greater detail below. Referring first to FIG. 3, the septum 10 of FIGS. 1 and 2 is shown in an isolated perspective view. The septum 10 generally includes three regions: a proximal portion 50, a distal portion 60, and a cavity portion 70. In some embodiments, either or both of the proximal and distal portions 50, 60 may be pre-slit to facilitate positioning of an introducer needle (not shown) in the assembly 20. Here, the distal portion 60 is shown with a slit 62. The cavity portion 70 is generally located centrally between the proximal and distal portions 50, 60. The cavity portion 70 generally serves to provide a region of reduced friction placed on the needle. In the embodiment of the septum 10 of the present invention, the cavity portion 70 extends completely through the proximal portion 50 and exits the proximal portion 50 of the septum 10 at a proximal outlet 72.

Figure 4:
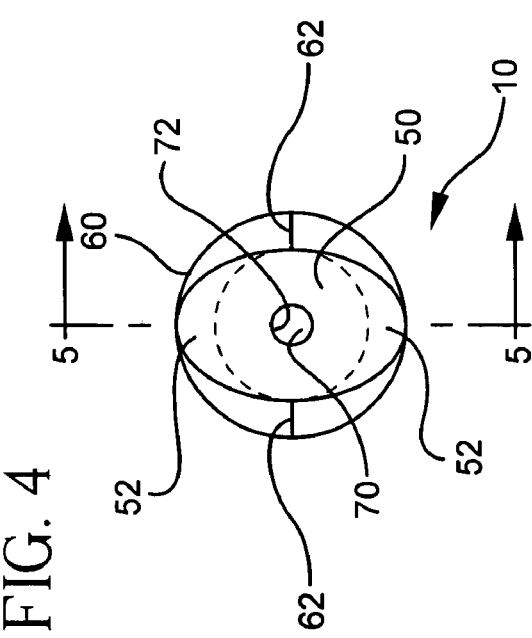
FIG. 4 is an end view of the one-piece low drag septum of FIG. 3.
Figure 6:
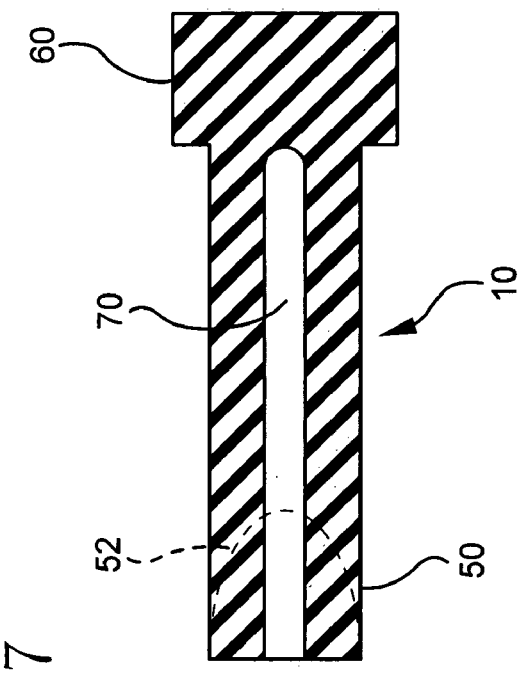
FIG. 6 is an end view of the one-piece low drag septum of FIG. 3 rotated 90 degrees.
Figure 7:
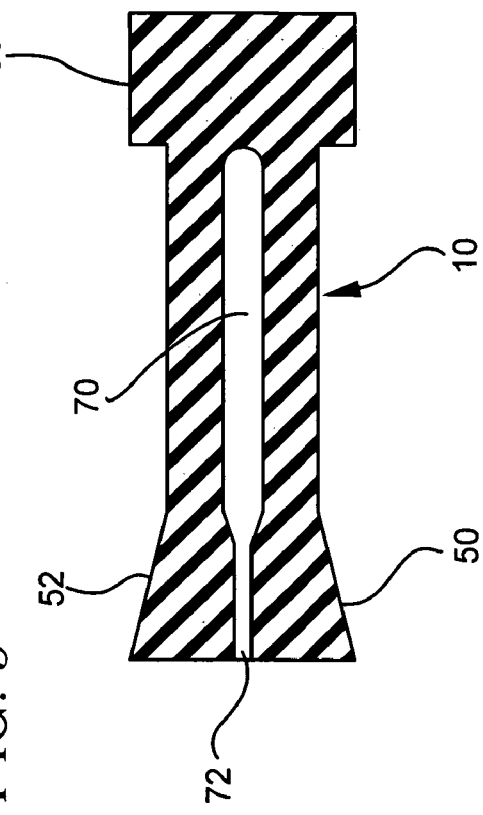
FIG. 7 is a cross-sectional view of the one-piece low drag septum of FIG. 3 taken at line 7-7 of FIG. 6.

In the septum 10 illustrated in FIG. 2 and FIGS. 3-7, the proximal portion 50 of the septum 10 includes at least one flared region 52. Referring to FIG. 3, the septum 10 of these figures includes a pair of flared regions 52 placed substantially opposite each other on the proximal portion 50 of the septum 10. The end view of the septum 10 presented in FIGS. 4 and 6 illustrates the relative shape and size of the proximal end 50 of the septum 10 relative to the distal end 60 prior to installation of the septum 10. Specifically, the flared regions 52 have dimensions that make the outer diameter of the septum 10 larger than the inner diameter of the septum housing 40 or catheter adapter 24, whichever is used to enclose the septum 10. During production of the catheter assembly 18, the septum 10 is forced into position within either the septum housing 40 and/or the catheter adapter 24. Installation of the septum 10 into the septum housing 40 or catheter adapter 24 compresses the flared regions 52. The compression of the flared regions 52 closes the proximal outlet 72, allowing it to act as a seal. FIGS. 6 and 7 provide end and cross-sectional views of the septum 10 of FIGS. 3-5 rotated by 90 degrees from the views of FIGS. 4-5. This further illustrates the shape of the flared regions 52.

Figure 8:
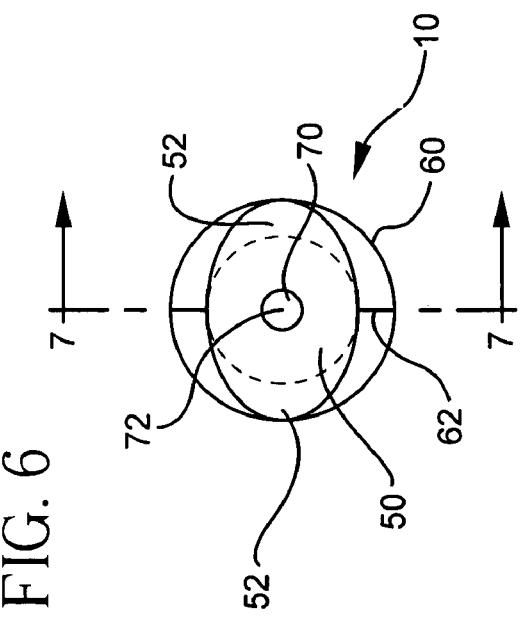
FIG. 8 is an end view of an alternative embodiment of the one-piece low drag septum of the invention similar to that illustrated in FIG. 3.
Figure 9:
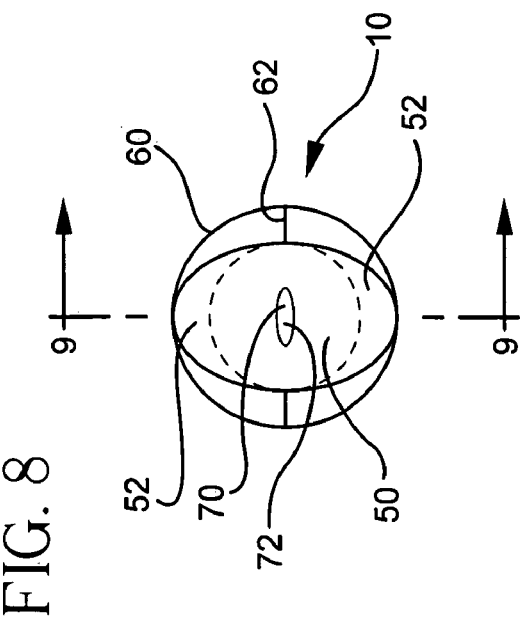
FIG. 9 is a cross-sectional view of the one-piece low drag septum of FIG. 8.

When injection molding is utilized to form the septum 10 of the present invention, the proximal outlet 72 may be produced by a core pin. A wide variety of shapes and geometries are possible for such core pins in the art, as known to one of ordinary skill in the art. Thus, although as illustrated in FIG. 2, the proximal outlet 72 has a round profile, its shape may be varied within the scope of the invention. Since the proximal outlet 72 of FIG. 2 is round, pressure exerted on it by the compression of the flared regions 52 flattens the opening to close it. The closed outlet 72 in this instance has a straight-line profile. Different outlet 72 geometries will potentially result in different characteristics of the closed outlet 72. One such alternative is illustrated in FIGS. 8 and 9, in which the cavity portion 70 has a shape that is narrowed at the point where it travels through the proximal portion 50 of the septum 10. In addition, as shown in FIG. 8, the cavity portion 70 has a cross-section resembling a flattened circle. Such a cross-section may facilitate sealing of the proximal outlet 72.

Figure 11:
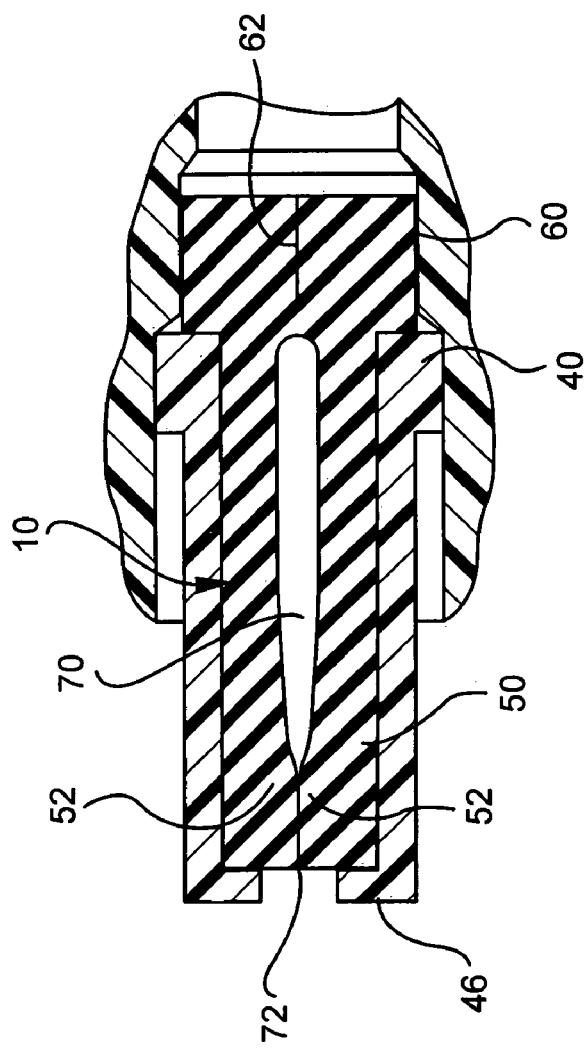
FIG. 11 is a cross-sectional view of the one-piece low drag septum of FIG. 3 placed within a septum housing and taken as at line 11-11 of FIG. 10.
Figure 10:
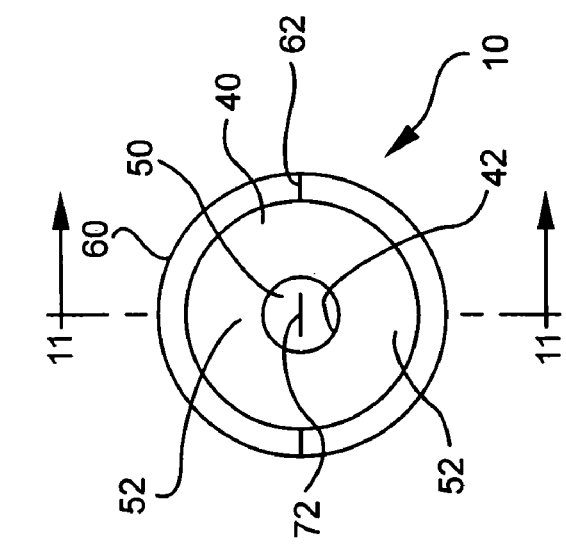
FIG. 10 is an end view of the one-piece low drag septum of FIG. 3 placed within a septum housing.

Referring next to FIGS. 10 and 11, a septum 10 is shown installed into a septum housing 40 which is, in turn, placed within a catheter adapter 24. As discussed above, catheter adapters may alternatively be constructed to receive the septum 10 directly without the intervention of the septum housing 40. The proximal portion 50 of the septum 10 is shown to have deformed to seal the proximal outlet 72 and the cavity portion 70. In the septum 10, the distal portion 60 of the septum 10 is generally configured to act as a primary seal for the assembly 20 by compressing tightly about an introducer needle during storage, and then, when the needle is withdrawn, closing tightly radially about the needle to prevent escape of fluid. The proximal portion 50 of the septum 10 acts as a secondary seal to close the cavity portion 70 of the septum 10. In some embodiments, the proximal portion 50 of the septum 10 may act as a squeegee to wipe fluid from the needle as it is withdrawn through the septum 10. The septum 10 may be made of a variety of suitable materials including, but not limited to thermoplastic elastomers such as polyisoprene or thermoset elastomers such as silicone.

The septum housing 40 shown in FIG. 11 has an open proximal end and an open distal end. The housing 40 surrounds at least a portion of the proximal portion 50 of the septum 10, and may enclose the distal portion 60 of the septum 10 in an interference fit to hold the septum 10 in place in position within catheter adapter 24. Alternatively, septum 10 could be located in catheter adapter 24 without the use of housing 40. Use of a septum housing 40 may in some instances ease installation of the septum 10 into the catheter adapter 24. As shown in FIG. 11, the septum housing 40 extends only along a part of the distal portion 60 of the septum 10. The housing 40 could alternately extend completely along the length of the septum 10 or just along the distal portion 60 of the septum 10. In such alternative configurations, it would be understood that housing 40 would apply a compressive force to septum 10 instead of the catheter adapter 24 as discussed below. The open proximal and distal ends of the septum housing 40 allow an introducer needle (not shown) to extend through the septum 10 and past the housing 40. In some embodiments it may be useful to provide a lip 46 at a proximal end of the housing 40 to partially extend over the face of the proximal end 50 of the septum 10. This may prevent attachment of another medical device to the proximal end 50 of catheter adapter 24.

Figure 12:
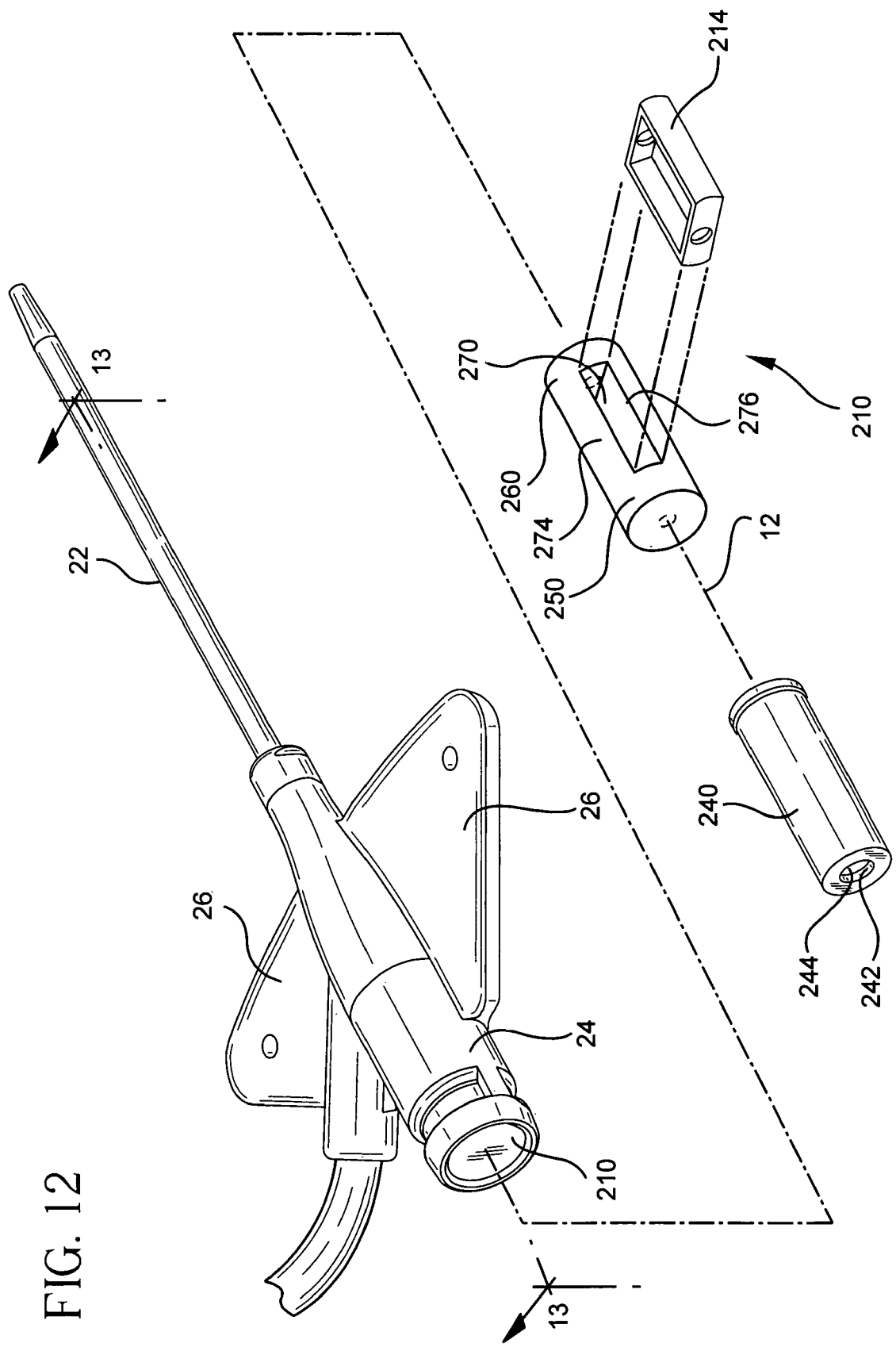
FIG. 12 is a partially-exploded perspective view of a catheter and introducer needle assembly using another septum of the present invention.

Referring next to FIG. 12, still another embodiment of the one-piece low drag septum 210 of the present invention is shown. As in the previous embodiments, the septum 210 includes a proximal end 250, a distal end 260, and a cavity portion 270. In this septum 210, however, the cavity portion 270 extends through at least one portion of the cavity wall 274. Indeed, in the embodiment of the septum 210 of the present invention, the cavity 270 extends completely through the septum 210. Such septa 210 must be installed in a septum housing 240 that encloses at least a portion of both the proximal and distal ends 250, 260 of the septum 210. This assures that the cavity portion 270 is sealed.

Septum 210 may be produced in a variety of ways, including, but not limited to, injection molding with a side-entry core pin. In such methods, a mold is designed to produce the proper septum shape and to receive a core pin entering from the side and extending into the mold at least up to and including the longitudinal axis 212. The shape of the core pin may be widely varied to change a profile 276 of the cavity portion 270. As illustrated in FIG. 12, the profile 276 is a substantially rectangular profile. A large variety of potential profiles 276 are included within the scope of the present invention, however, including, but not limited to, oval, round, and others known to one of ordinary skill in the art.

In some embodiments of the present invention, it may be beneficial to provide a stiffener 214 for the septum 210 to facilitate its installation into a septum housing 240. Such a stiffener may be an element designed to conform to the cavity portion 270 of the septum to provide longitudinal stiffness, such as by extending from a proximal end of the cavity portion 270 to a distal end of the cavity portion 270. In some cases, the stiffness of the polymer used to produce the septum 210 provides sufficient stiffness without additional components. In septa 210 in which the cavity portion 270 extends only through a single portion of the cavity wall 274, the cavity wall 274 may retain sufficient stiffness to avoid the need for a stiffener.

As with the previous embodiments of the septum of the present invention, septum 210 of FIG. 12 may be pre-slit to facilitate insertion of an introducer needle (not shown) therethrough. Such preparation is known to those of ordinary skill in the art.

Figure 15:
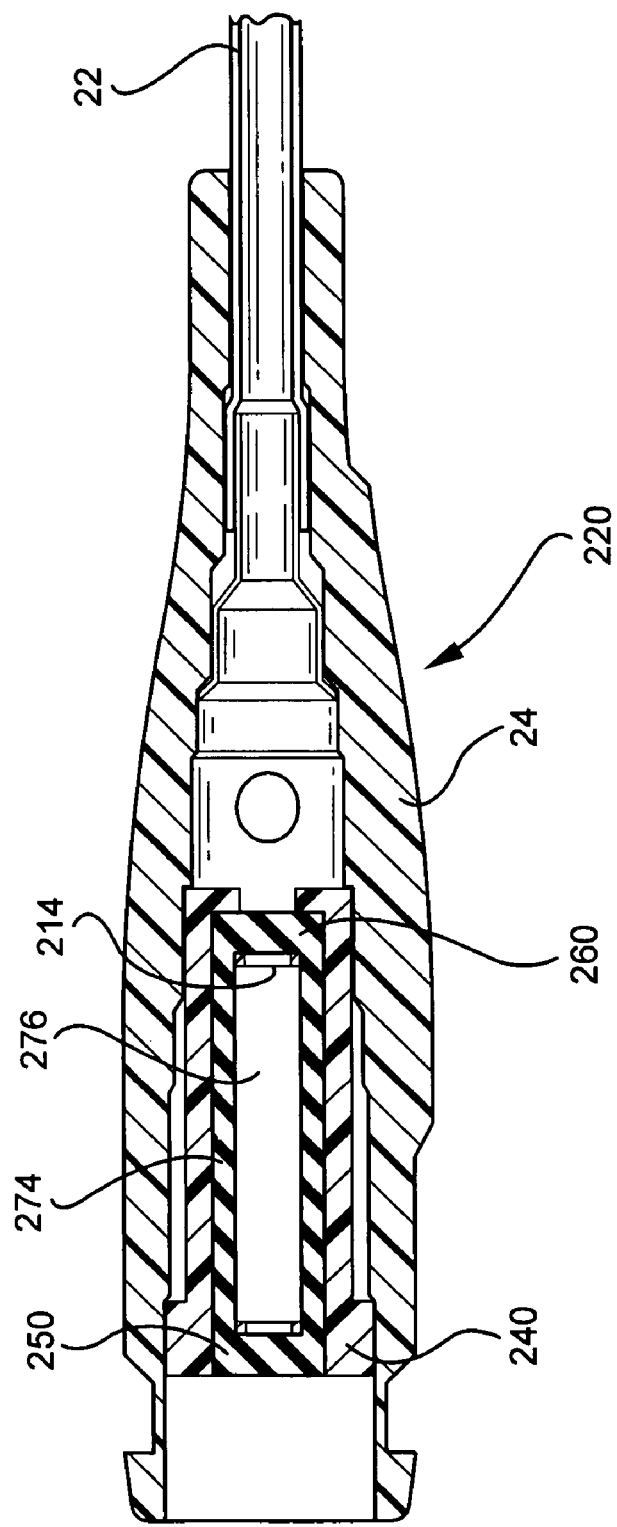
FIG. 15 is a cross-sectional view of the catheter and introducer needle assembly of FIGS. 12-14 assembled and taken at line 13-13 of FIG. 12 with the introducer needle completely removed.

During storage and use of the catheter adapter 24, the proximal and distal portions 250, 260 of the septum 210 conform to the outer diameter of the needle 230, as illustrated in FIG. 13. Thus, as the adapter 210 is inserted into a patient, the septum prevents leakage of fluid from between the needle (not shown) and the catheter 22 into the adapter 24. Once the needle 230 has been partially removed, however, as illustrated in FIG. 14, each portion of the septum 210 closes in turn to seal the catheter adapter. In FIG. 14, the distal portion 260 is shown to have closed as the distal tip 34 of the needle 230 was removed into the cavity 270. FIG. 15 shows the needle 230 completely removed from the septum 210 such that the proximal and distal portions 250, 260 are sealed shut.

Figure 16:
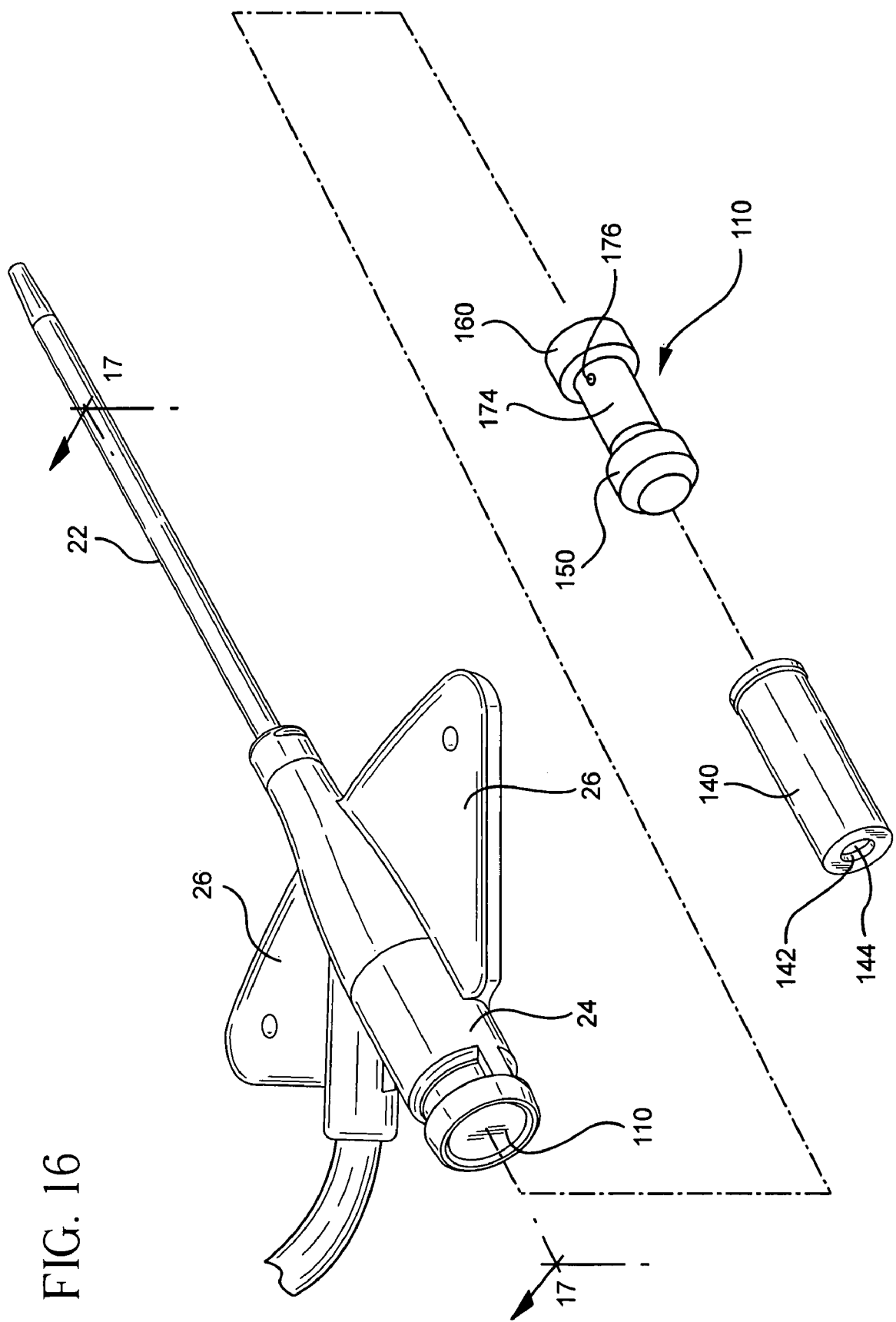
FIG. 16 is a partially-exploded perspective view of a catheter and introducer needle assembly using another septum of the present invention.

Referring next to FIG. 16, a partially-cutaway view of another embodiment of the one-piece low drag septum 110 of the present invention is shown. This septum 110 similarly includes a proximal portion 150, a distal portion 160, and a cavity portion. In this case, although the cavity 170 is shown to potentially extend into the proximal and distal portions 150, 160, it does not penetrate them. As a result, the proximal and distal ends 150, 160 may be pre-slit to facilitate insertion of an introducer needle (not shown) therethrough, or such a needle may simply be inserted through the material of the septum 110. This septum 110 may be produced using an injection molding technology such as, but not limited to, gas-assist injection molding.

Gas-assist injection molding is a technology similar to traditional injection molding techniques in which a molten polymer is introduced into a mold under pressure to produce an object. In gas assist technologies, however, injection of the molten polymer is followed by injection of a pressurized gas into the mold. The injected gas forms a bubble that acts to drive the polymer into the extremities of the mold and then remains in the completed product as an open space. In some instances, gas-assist injection molding is used to create molded objects that require an open internal space. Construction of the septum 110 in this manner provides a hollow cavity portion (not shown) to the septum 110 without the use of a core pin.

It should be noted that in objects produced using injection molding methods, including gas-assist injection molding, there may be a visible entry point 176 at the point where the mold gate 116 intersects with the object (here a cavity wall 174 of the septum 110). This entry point 176 may become visible when the mold gate 116 and runner 114 are removed from the finished product. In the instance of the septum 110, this entry point 176 may range in appearance from a simple blemish or surface imperfection to a small hole penetrating the cavity wall 174. Thus, within the scope of the invention the mold gate 116 and entry point 176 are placed on the septum 110 to preserve sealing function even when the entry point 176 is a complete hole. In the septum 110 illustrated in FIG. 16, the entry point 176 is placed on the cavity wall 174 such that even should the wall be completely penetrated, if a fluid were to escape the cavity 170, it would be prevented from leaking into the environment by the seal produced between the proximal region 150 of the septum 170 and the septum housing 140.

Figure 17:
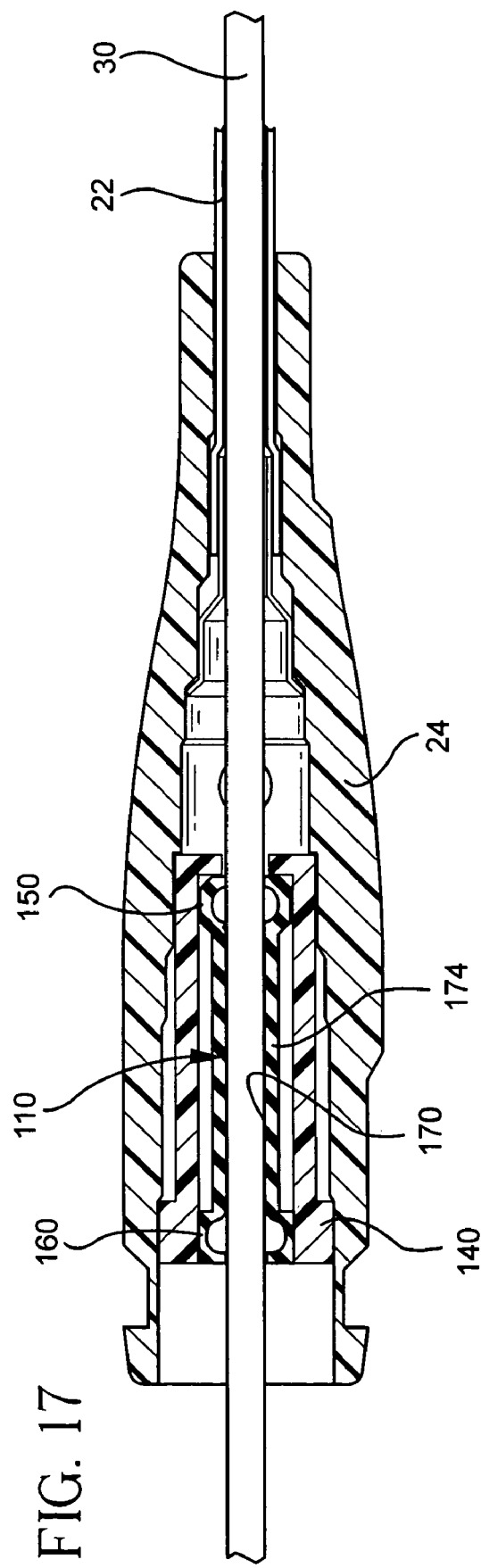
FIG. 17 is a cross-sectional view of the catheter and introducer needle assembly of FIG. 16 assembled and taken at line 17-17 of FIG. 16 with the introducer needle in place.
Figure 18:
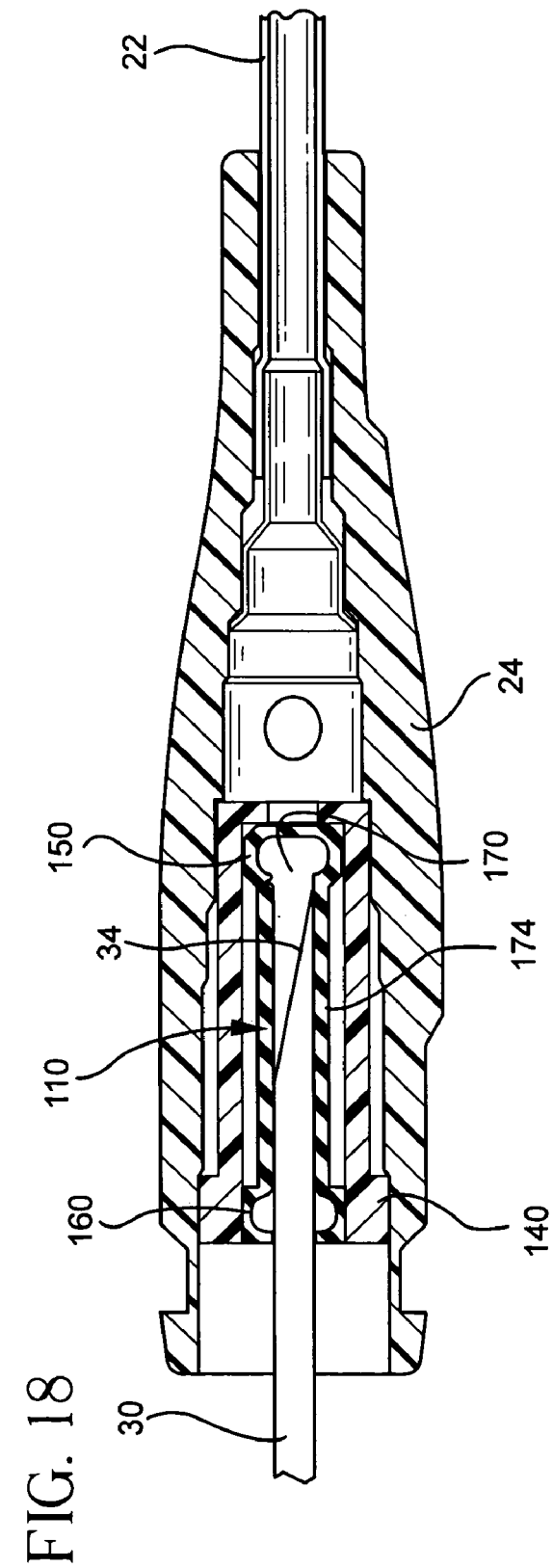
FIG. 18 is a cross-sectional view of the catheter and introducer needle assembly of FIGS. 16 and 17 assembled and taken at line 17-17 of FIG. 16 with the introducer needle partially removed.

As with the previously-discussed embodiments of the septum of the invention, as illustrated in FIG. 17, when the needle 130 penetrates both the proximal and distal portions 150, 160 of the septum 110, the septum 110 conforms to the needle 130. Similarly, when the needle 130 is withdrawn, as partially shown in FIG. 18, the septum 110 seals shut, as seen on the distal portion 160 of the septum 110.

Figure 19:
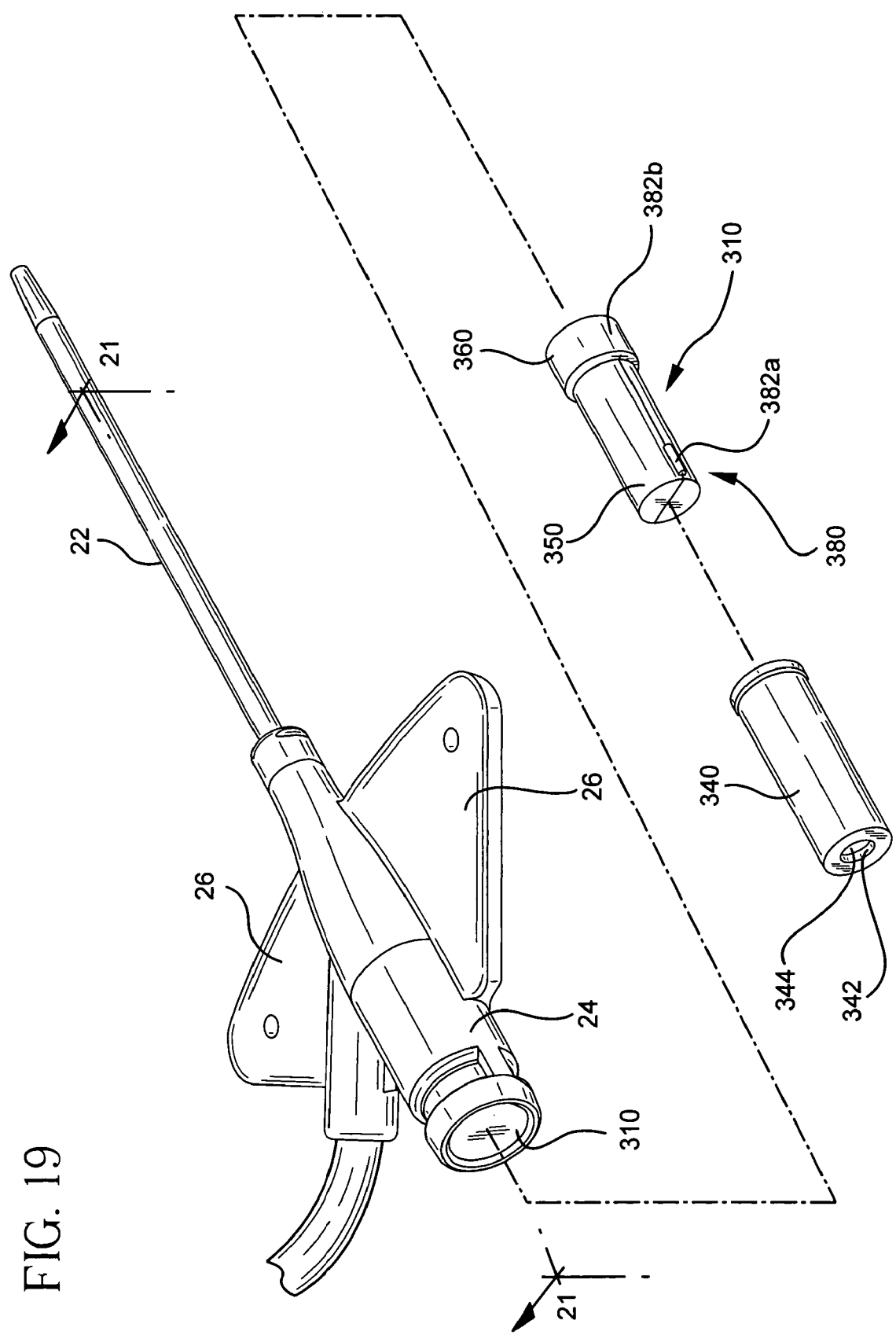
FIG. 19 is a partially-exploded perspective view of a catheter and introducer needle assembly using another septum of the present invention.

FIGS. 19-22 provide a series of perspective and cross-sectional views of another embodiment of the one-piece low drag septum 310 of the invention as it is assembled about an introducer needle 330 and placed in a catheter and introducer needle assembly 320. FIG. 19 provides a partially exploded perspective view of the septum 310 as it would be assembled and placed within a catheter and introducer needle assembly. As with the previously-discussed embodiments, septum 310 has a proximal end 350, a distal end 360, and a cavity portion 370. Each of these components of this septum 310, however, is made up of a plurality of fractional segments which swing together with a hinge 380. In some embodiments, the hinge 380 is composed of a plurality of segments, as in FIGS. 19-22, in which the hinge 380 includes a proximal hinge region 382a and a distal hinge region 382b. During assembly, the fractional segments of the components of the septum 310 are swung together while held in proper relationship by the hinge 380. As illustrated in FIGS. 14-17, the fractional segments of the septum 10 may be evenly divided, i.e., the segments illustrated in FIGS. 14-17 are each substantially equal halves of the septum 310. As understood by one of ordinary skill in the art, many other fractional divisions linked by hinges may be provided within the scope of the invention.

Figure 20:
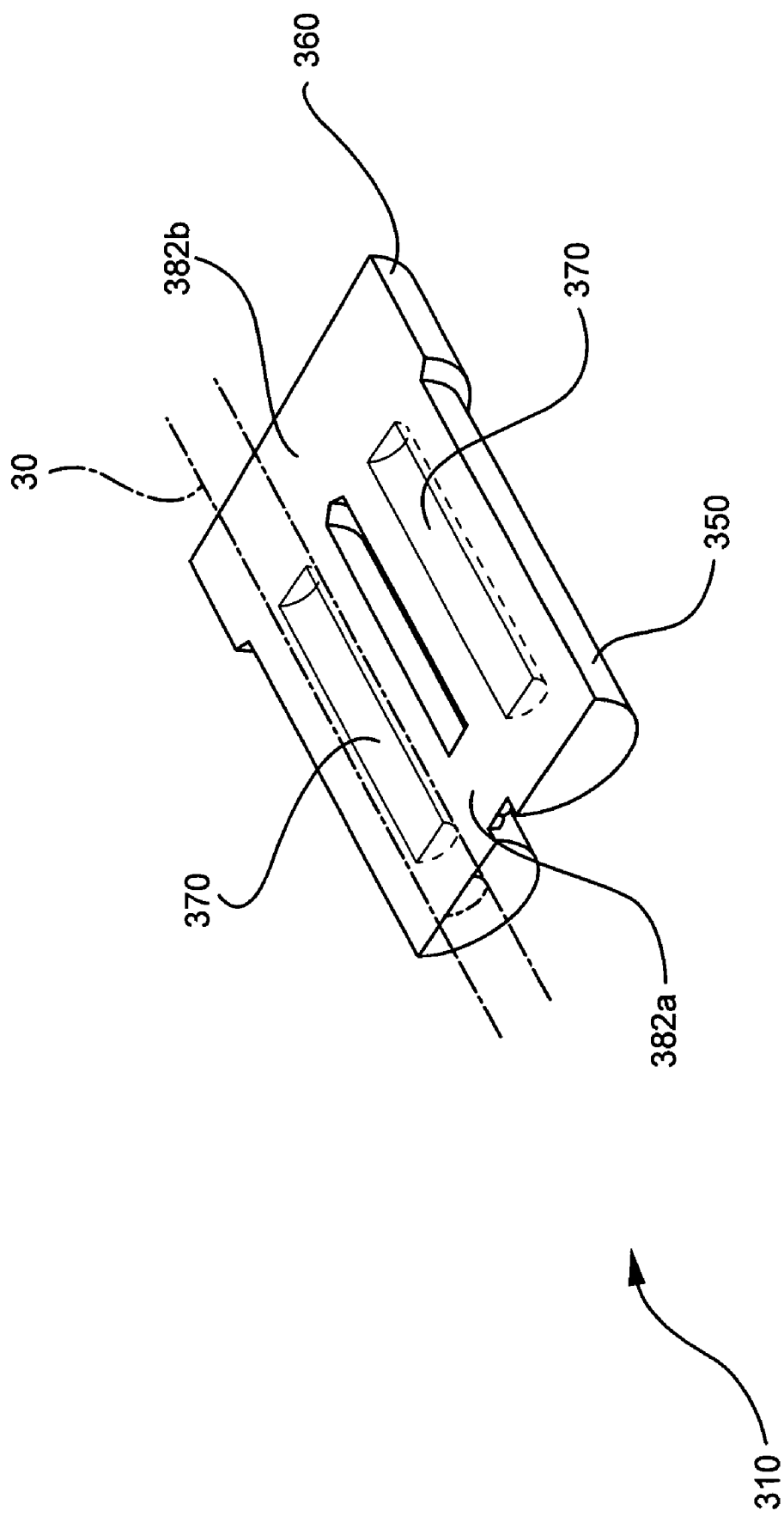
FIG. 20 is a perspective view of the septum illustrated in FIG. 19 shown prior to its placement about an introducer needle.

The septum 310 may be assembled about an introducer needle 30 as illustrated in FIG. 20. Alternately, the septum 310 may be folded first and the needle subsequently inserted through the septum 310. This septum 310 simplifies assembly by avoiding the need to provide slits in the proximal and distal portions 350, 360 to allow insertion of the needle through the septum 310.

Figure 21:
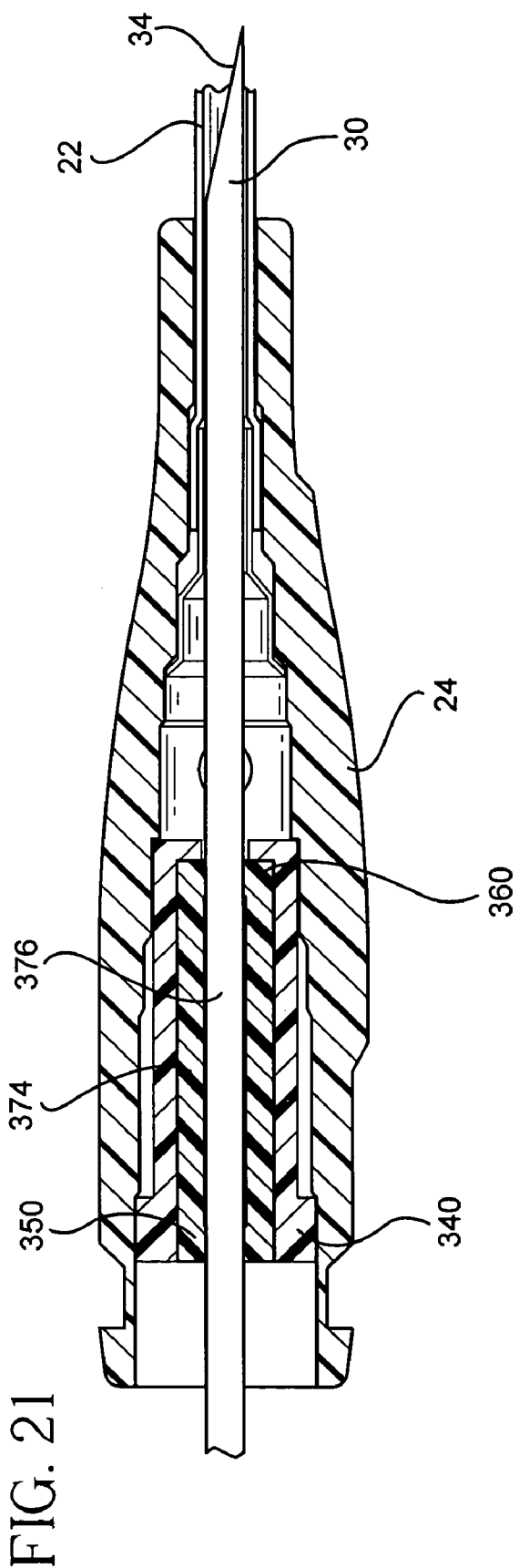
FIG. 21 is a cross-sectional view of the catheter and introducer needle assembly of FIG. 19 assembled and taken at line 21-21 of FIG. 19 with the introducer needle in place.

As with the previously-discussed embodiments of the septum of the present invention, it may be useful to provide a septum housing 340 for use with the septum 310 as illustrated in FIG. 21. In this embodiment of the septum 310, it may be useful to assist in retaining the hinged segments of the septum 310 in proper alignment. Such a septum housing 340 may be threaded about the introducer needle 330 and the septum 310 after assembly of the septum 310 about the needle 310 or after folding of the septum 310 but prior to insertion of the needle 330 therethrough.

Figure 22:
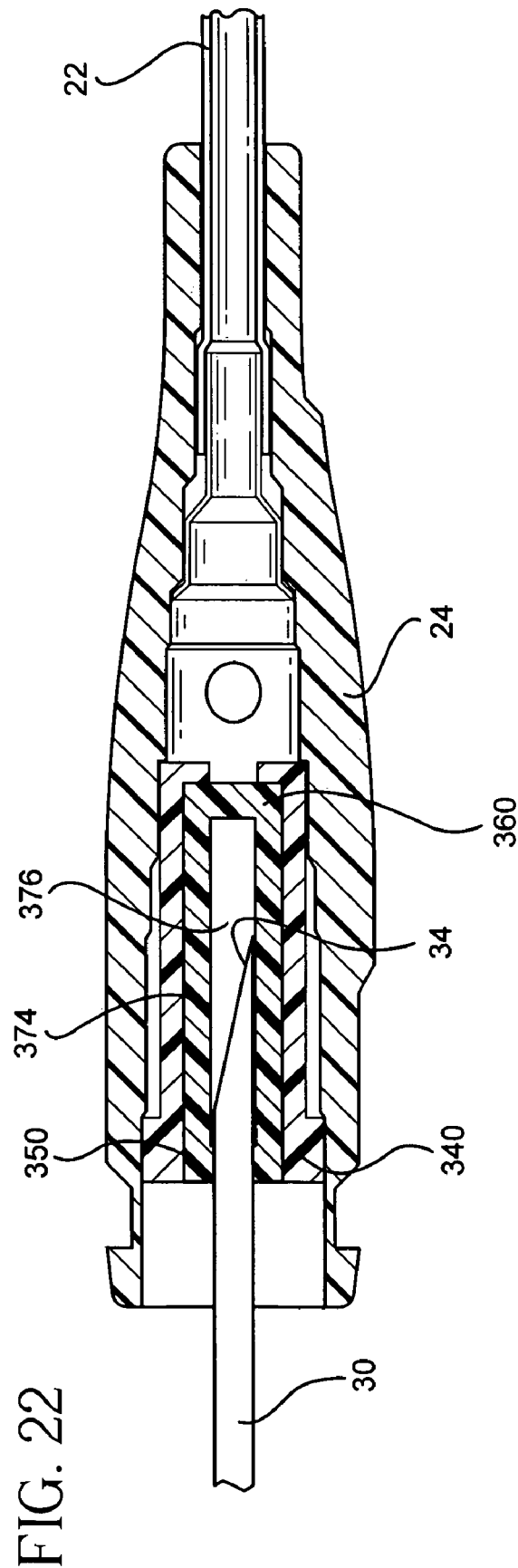
FIG. 22 is a cross-sectional view of the catheter and introducer needle assembly of FIGS. 19 and 20 assembled and taken at line 20-20 of FIG. 19 with the introducer needle partially removed.

FIGS. 21 and 22 illustrate the septum 310 as it appears when placed within a septum housing 340 and placed within a catheter and introducer needle assembly 320 with a catheter adapter 24 and a catheter 22. The route of the introducer needle 330 through the cavity 370 of the septum 310 is also visible. FIG. 21 shows the configuration of the septum 310 when the introducer needle 330, i.e., when the catheter and introducer needle assembly 320 is either in storage or initial use. FIG. 22 shows the configuration of the septum 310 when the needle 330 has been partially removed, such that the distal portion 360 of the septum 310 has closed and the distal tip 34 of the needle 330 has been withdrawn into the cavity 370 of the needle 330. The proximal tip 350 seals in a similar manner following complete withdrawal of the needle 330 from the assembly 320.

Figure 23:
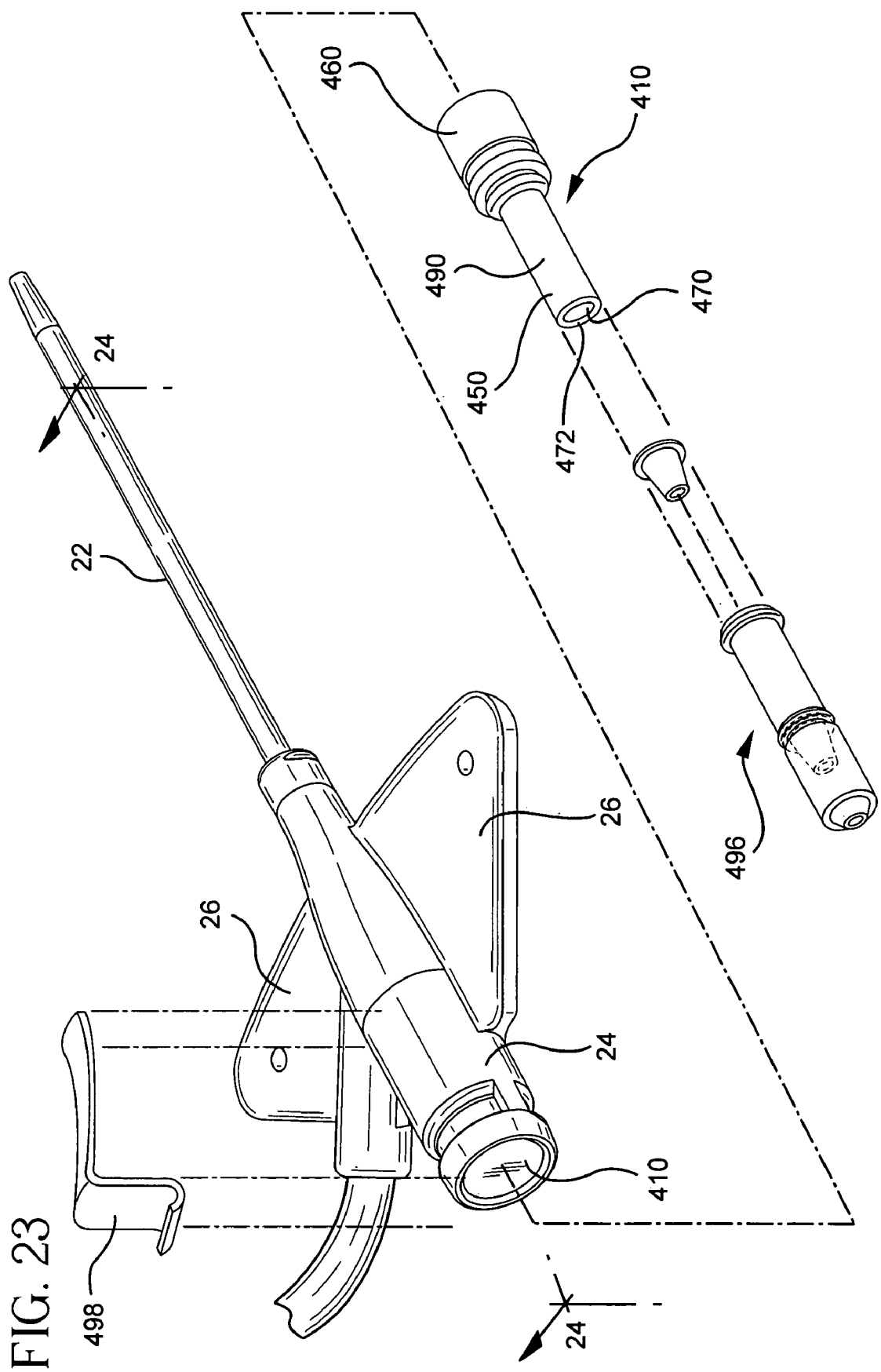
FIG. 23 is a partially-exploded perspective view of a catheter and introducer needle assembly using another septum of the present invention.
Figure 24:
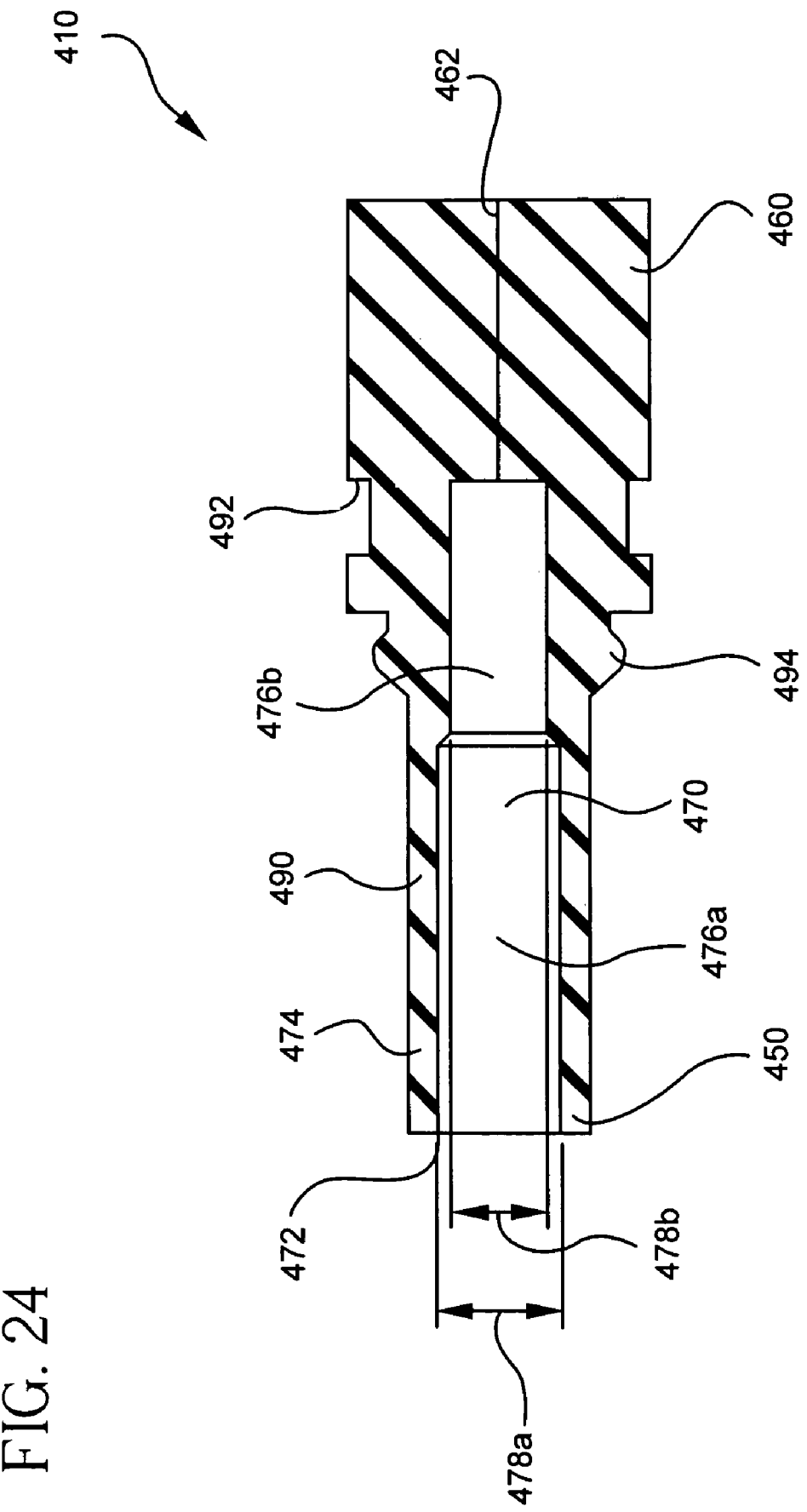
FIG. 24 is a perspective view of the septum of FIG. 23
Figure 25:
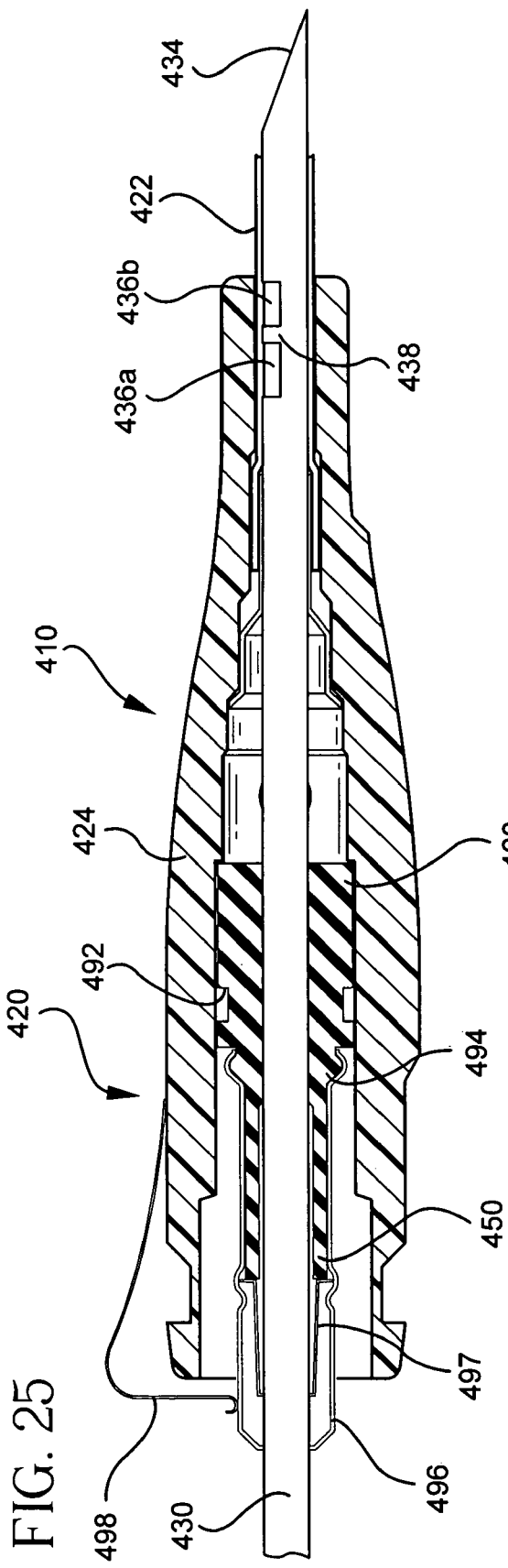
FIG. 25 is a cross-sectional view of the catheter and introducer needle assembly of FIG. 23 with the introducer needle in place.

FIGS. 23-25 are a series of views of yet another one-piece low drag septum 410 of the present invention shown first isolated in a partially-exploded perspective view of a catheter and introducer needle assembly 420, and then in cross-section. In FIG. 23, the septum 410 is shown in an isolated perspective view, having been exploded from its place within the catheter and introducer needle assembly 420. The septum 410 includes a proximal portion 450, a distal portion 460, and a cavity portion 470. The distal portion 460 resembles those of other embodiments of the septum 410 of the present invention discussed above, and may include a slit 462 to facilitate insertion of an introducer needle (not shown) therethrough. The proximal portion 450 comprises an elongated sheath extending from the distal portion 460 to surround an introducer needle (not shown) traveling therethrough. This sheath is, in effect, an extension of the cavity wall 474.

Figure 26:
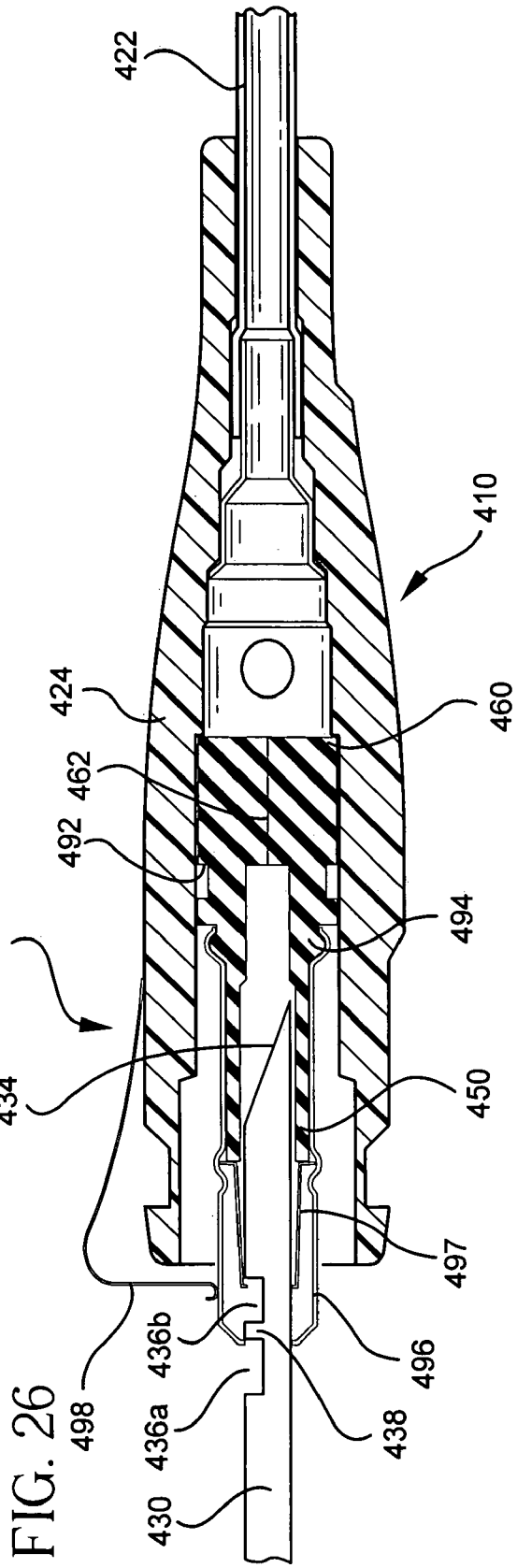
FIG. 26 is a cross-sectional view of the catheter and introducer needle assembly of FIGS. 23 with the introducer needle partially removed.

FIG. 24 illustrates that the cavity portion 470 of the septum 410 differs from those previously disclosed. Like the septum 10 illustrated in FIGS. 2-11, the cavity portion 470 of septum 410 shown in FIG. 24 extends completely through the proximal portion 450 of the septum 410, opening to the environment at a proximal outlet 472. Unlike this embodiment, however, as seen in FIGS. 25 through 27, the cavity portion 470 includes a distal cavity 476b and a proximal cavity 476a. The distal cavity 476b is positioned near the distal portion 460 of the septum 410. The distal cavity 476b has a distal inner diameter 478b, while the proximal cavity 476b has a proximal inner diameter 478a. In the septum 410, the distal inner diameter 478b of the distal cavity 476b is smaller than the outer diameter of an introducer needle used with the assembly 420. The proximal inner diameter 478a of the proximal cavity 476a, although larger than the distal inner diameter 478b, is still slightly smaller than the outer diameter of the introducer needle (not shown).

Due to their inner diameters 478a, 478b, the proximal and distal cavities 476a, 476b apply differing forces to the needle traveling through them. The small diameter 478b of the distal cavity 476b allows a strong force to be placed on the needle to cleanse it as it exits the distal portion 460 of the septum. The larger diameter 478a of the proximal cavity 476a reduces the force placed on the needle by the septum 410, thus reducing drag on the needle, but continues to act as a squeegee, cleansing the needle as it exits. As with the previously-discussed septum above, upon withdrawal of the needle, the septum 410 seals shut.

FIG. 25 is a cross-sectional view of the septum 410 installed within a catheter and introducer needle assembly 420. The assembly 420 further includes an introducer needle 430 which passes through the septum 410. The needle 430 includes a distal tip 434 with a flashback notch 436a and a locking notch 436b. The needle 430 may further include a ridge 438 to interact with the needle shielding device 496. The assembly 420 may additionally include a closure 498 adapted to block reentry of the needle 430 into the assembly 420 after a single removal.

In the septum 410 illustrated in FIG. 25, the cavity wall 474 may optionally include a variety of additional features on its outer surface 490. One such feature is a groove 492 to facilitate attaching the septum 410 to a catheter adapter 424 as shown in FIG. 25. Another such feature is an interlock feature 494 useful in the embodiment of the septum 410 illustrated in FIGS. 25-27 to attach a needle shielding device 496 and retainer 497 also shown. The needle shielding device 496 interacts with retainer 497 to cover the distal tip 434 of the needle 430 when it has been withdrawn from the septum 410.

FIG. 26 shows the needle 430 being partially removed from the assembly 420. More specifically, in FIG. 20, the tip of the needle 430 has passed through the distal portion 460 of the septum 410. Note that as described above, the length of the septum 410 is such that the flashback notch 436a of the needle 430 has not exited the septum 410, thus preventing escape of fluid. At this stage of removal, the ridge 438 of the needle 430 engages the needle shielding device 496 provided about the septum 410 dislodging the device 496 from the septum and causing it to travel with the needle 430 as it is withdrawn. FIG. 27 illustrates that when the needle 430 is completely withdrawn from the assembly 420, the shielding device 496 encompasses the distal tip 434 of the needle 430, protecting a user from potential needlestick injury. At the same time, the closure 498 has closed down over the opening in the assembly 420 through which the needle 430 traveled into the septum 410. This prevents re-use of the device by blocking reinsertion of a needle.

The instant invention provides a one-piece septum for providing a seal about a needle used in a catheter and introducer needle assembly during storage and use, and then subsequently sealing the assembly upon withdrawal of the needle after initial use. The various embodiments of the septum of the present invention are all susceptible to being produced using rapid injection molding techniques. Each includes a distal portion which acts as a primary seal against fluid flow from a patient, a distal seal which acts as a secondary seal and in some cases a needle cleaner, and a cavity. The septum of the present invention is long enough to adequately enclose needles with notches that act to confirm entry into a blood vessel, but also include an inner cavity to reduce the amount of drag placed on the needle by the septum.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A septum assembly for providing a seal about a needle and for sealing closed when the needle is withdrawn, the septum assembly comprising:
    a septum housing;
    a one-piece septum inserted within the septum housing, the septum having a longitudinal axis, a distal portion, a distal outlet, a proximal portion, a proximal outlet, and a cavity portion disposed between the distal portion and the proximal portion wherein the proximal portion of the one-piece septum comprises at least two flared regions extending outwardly away from an outer diameter of the proximal portion of the septum such that when the septum is placed within the housing the housing exerts a compressive force on the flared regions sealing the proximal outlet; and
    wherein the distal end of the septum includes a slit substantially sealing the distal outlet.

2. The septum assembly of claim 1, wherein the cavity portion extends completely through the proximal portion of the septum.

3. The septum assembly of claim 1, wherein the at least two flared regions extends away from an outer diameter of the proximal portion of the septum along substantially all of the outer diameter of the proximal portion of the septum.

4. A needle-sealing assembly comprising:
    a needle having a proximal end, a distal end with an opening, and an outer diameter;
    a housing having a predetermined shape, the needle being disposed within the housing;
    a one-piece seal disposed within the housing about the needle and having a longitudinal axis, a distal portion, a proximal portion, and a cavity portion, the cavity portion extending between the proximal portion and the distal portion and having an inner diameter greater than or equal to the outer diameter of the needle, wherein the cross section of the cavity portion seals a proximal outlet and a distal outlet of the one piece seal when the needle is withdrawn from the one-piece seal wherein the proximal portion of the one-piece septum comprises two flared regions extending outwardly away from an outer diameter of the proximal portion of the septum such that when the septum is placed within the housing the housing exerts a compressive force on the flared regions sealing the proximal outlet, wherein the two flared regions are positioned substantially opposite each other on the outer diameter of the proximal portion of the seal.

5. A method of sealing a catheter adapter during the storage, use, and removal of a needle projecting therethrough, the method comprising the steps of:
    providing a catheter adapter having a housing and including an introducer needle extending therethrough, the needle having a proximal end, and a distal end with bore;
    providing a one-piece elastomeric septum disposed about the needle and positioned within the housing, the septum having a cavity portion provided between a proximal septum portion and a distal septum portion of the septum, the cavity portion having an inner diameter greater than or equal to the outer diameter of the needle wherein the proximal portion of the one-piece septum comprises at least two flared regions extending outwardly away from an outer diameter of the proximal portion of the septum such that when the septum is placed within the housing the housing exerts a compressive force on the flared regions sealing the proximal outlet, wherein the two flared regions are positioned substantially opposite each other on the outer diameter of the proximal portion of the seal; and wherein the cavity portion has a cross section that facilitates sealing of a proximal and distal outlet of the one piece elastomeric septum when the introducer needle is withdrawn from the catheter adapter.

6. The method of sealing a catheter adapter of claim 5, wherein the introducer needle further comprises a notch adjacent the opening of the distal end and a notch distance defined as the distance between the notch and a distal end of the opening in the distal end of the introducer needle, and wherein the septum has an overall length greater than the notch distance.

* * * * *